(12) United States Patent
Natan et al.

(10) Patent No.: US 11,908,130 B2
(45) Date of Patent: Feb. 20, 2024

(54) APPARATUSES AND METHODS FOR DIGITAL PATHOLOGY

(71) Applicant: Protein Metrics, LLC, Cupertino, CA (US)

(72) Inventors: Michael J. Natan, Weston, MA (US); Marshall Bern, San Carlos, CA (US); Eric Carlson, Cupertino, CA (US)

(73) Assignee: Protein Metrics LLC, Cupertino, CA (US)

( * ) Notice: Subject to any disclaimer, the term of this patent is extended or adjusted under 35 U.S.C. 154(b) by 529 days.

(21) Appl. No.: 17/139,882

(22) Filed: Dec. 31, 2020

(65) Prior Publication Data
US 2021/0209756 A1    Jul. 8, 2021

Related U.S. Application Data

(60) Provisional application No. 62/957,095, filed on Jan. 3, 2020.

(51) Int. Cl.
| | |
|---|---|
| *G06K 9/00* | (2022.01) |
| *G06T 7/00* | (2017.01) |
| *G06T 7/11* | (2017.01) |
| *G16H 10/40* | (2018.01) |
| *G16H 30/40* | (2018.01) |
| *G06N 20/00* | (2019.01) |
| *G01N 33/483* | (2006.01) |
| *G16H 70/60* | (2018.01) |

(52) U.S. Cl.
CPC ....... *G06T 7/0012* (2013.01); *G01N 33/4833* (2013.01); *G06N 20/00* (2019.01); *G06T 7/11* (2017.01); *G16H 10/40* (2018.01); *G16H 30/40* (2018.01); *G16H 70/60* (2018.01); *G06T 2207/10056* (2013.01); *G06T 2207/30024* (2013.01); *G06T 2207/30204* (2013.01)

(58) Field of Classification Search
CPC ............. G06T 7/0012; G06T 7/11; G06T 2207/10056; G06T 2207/30024; G06T 2207/30204; G16H 70/60; G16H 10/40; G16H 30/40; G06N 20/00; G01N 33/4833

See application file for complete search history.

(56) References Cited

U.S. PATENT DOCUMENTS

| | | | |
|---|---|---|---|
| 2012/0207360 A1* | 8/2012 | Mehanian | G06F 18/24 382/128 |
| 2013/0078624 A1* | 3/2013 | Holmes | G01N 35/00 73/61.52 |
| 2013/0301898 A1* | 11/2013 | Jain | G06T 7/11 382/133 |
| 2016/0253817 A1* | 9/2016 | Chen | G06V 20/695 382/133 |
| 2016/0341731 A1* | 11/2016 | Sood | G16B 40/00 |
| 2017/0154420 A1* | 6/2017 | Barnes | G06T 7/11 |
| 2017/0262984 A1* | 9/2017 | Barnes | G06V 20/698 |

(Continued)

*Primary Examiner* — Hadi Akhavannik
(74) *Attorney, Agent, or Firm* — Shay Glenn LLP

(57) ABSTRACT

Digital pathology is a promising alternative to manual slide analysis, but improvements in imaging and analysis methods are needed to provide an analysis data set of images that can easily be handled, stored, and importantly, delivered from one data location to another. Methods and software are described herein to improve image collection and analysis.

19 Claims, 20 Drawing Sheets
(18 of 20 Drawing Sheet(s) Filed in Color)

(56) References Cited

U.S. PATENT DOCUMENTS

| | | | |
|---|---|---|---|
| 2017/0270346 A1* | 9/2017 | Ascierto | G06T 7/0012 |
| 2018/0306768 A1* | 10/2018 | Little | G01N 21/6456 |
| 2018/0330498 A1* | 11/2018 | Little | G01N 21/6456 |
| 2019/0137497 A1* | 5/2019 | Thorne | C12Q 1/6886 |
| 2019/0220981 A1* | 7/2019 | Chen | G06V 20/695 |
| 2019/0295252 A1* | 9/2019 | Fuchs | G06T 7/0012 |
| 2020/0066407 A1* | 2/2020 | Stumpe | G06N 3/045 |
| 2021/0193323 A1* | 6/2021 | Jain | G16H 50/70 |
| 2022/0076411 A1* | 3/2022 | Georgescu | G06V 20/695 |

* cited by examiner

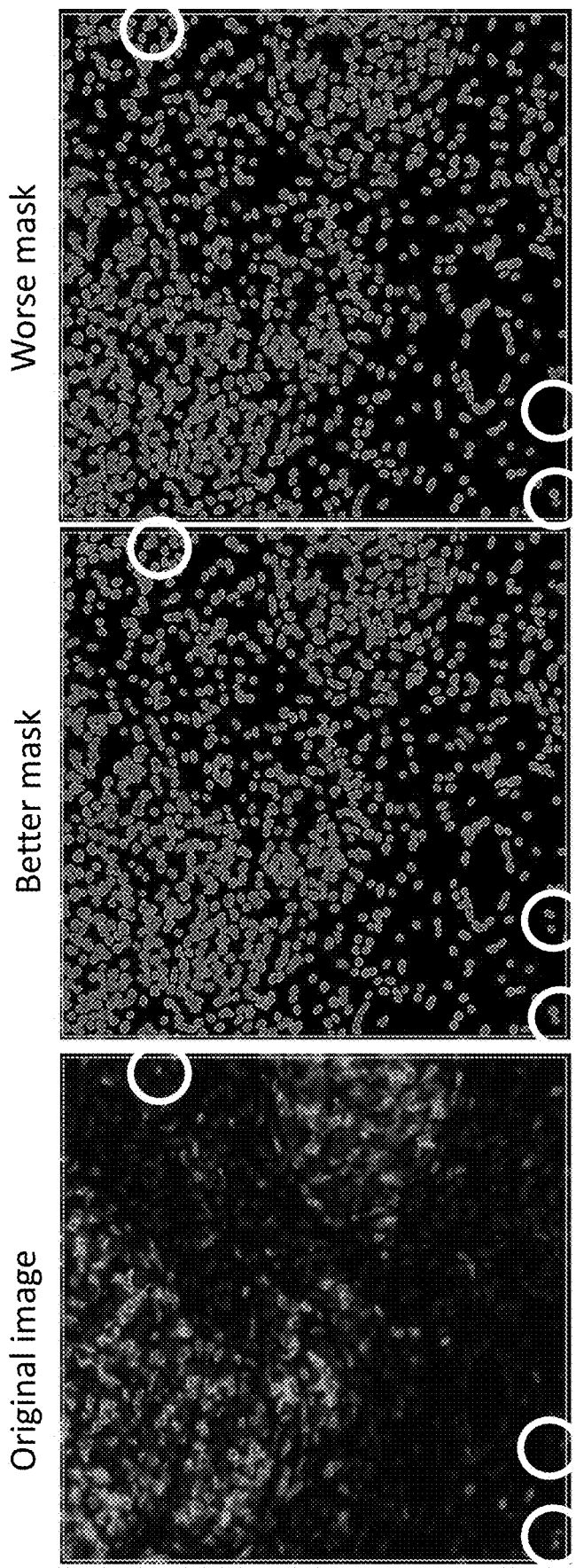

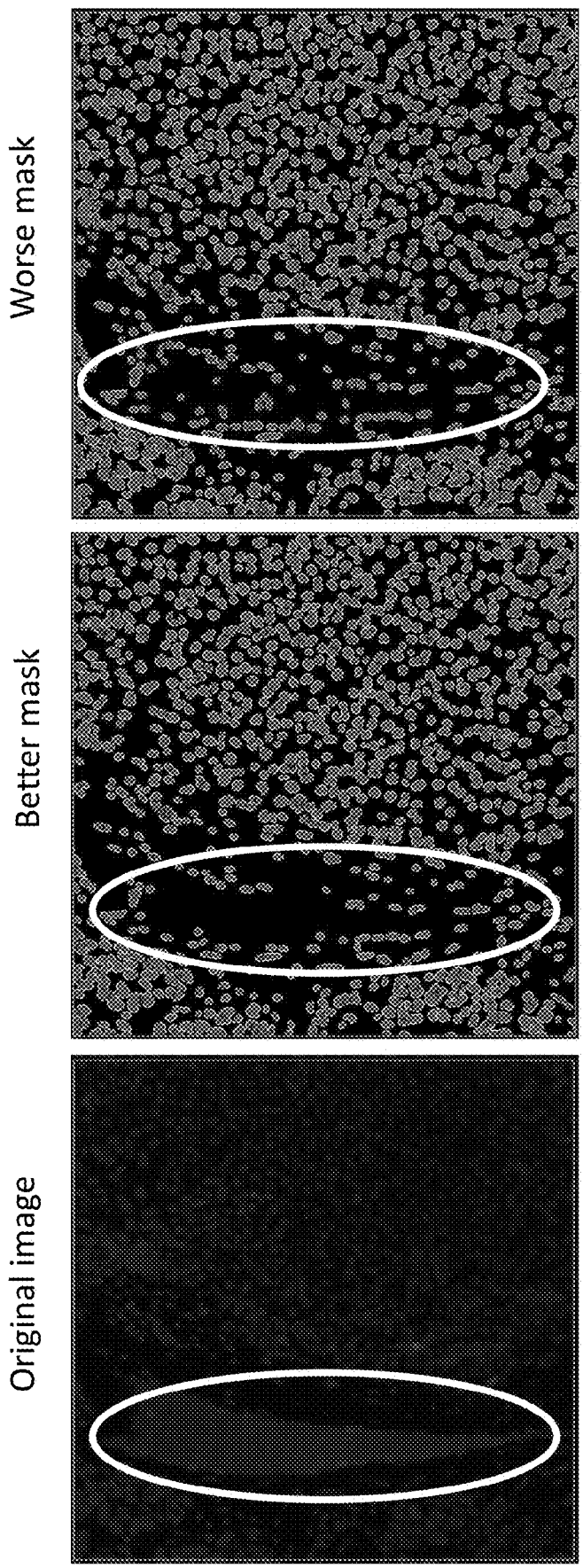

| Analysis | Nuclear Contrast Threshold | Minimum Nuclear Intensity | Threshold FITC | Rank ROI 1 | Rank ROI 2 |
|---|---|---|---|---|---|
| 1 | 0.504 | 0.052 | 900 | | 27 |
| 2 | 0.504 | 0.052 | 1050 | | 24 |
| 3 | 0.504 | 0.052 | 1200 | | 23 |
| 4 | 0.504 | 0.057 | 900 | | |
| 5 | 0.504 | 0.057 | 1050 | | |
| 6 | 0.504 | 0.057 | 1200 | | |
| 7 | 0.504 | 0.062 | 900 | | |
| 8 | 0.504 | 0.062 | 1050 | 26 | 4 |
| 9 | 0.504 | 0.062 | 1200 | 25 | 2 |
| 10 | 0.507 | 0.052 | 900 | | 26 |
| 11 | 0.507 | 0.052 | 1050 | 3 | |
| 12 | 0.507 | 0.052 | 1200 | 4 | |
| 13 | 0.507 | 0.057 | 900 | | |
| 14 | 0.507 | 0.057 | 1050 | | |
| 15 | 0.507 | 0.057 | 1200 | | 6 |
| 16 | 0.507 | 0.062 | 900 | | 5 |
| 17 | 0.507 | 0.062 | 1050 | | 3 |
| 18 | 0.507 | 0.062 | 1200 | | 1 |
| 19 | 0.51 | 0.052 | 900 | 2 | 25 |
| 20 | 0.51 | 0.052 | 1050 | 1 | |
| 21 | 0.51 | 0.052 | 1200 | 3 | |
| 22 | 0.51 | 0.057 | 900 | | |
| 23 | 0.51 | 0.057 | 1050 | | |
| 24 | 0.51 | 0.057 | 1200 | | |
| 25 | 0.51 | 0.062 | 900 | 23 | |
| 26 | 0.51 | 0.062 | 1050 | 24 | |
| 27 | 0.51 | 0.062 | 1200 | 27 | |

FIG. 12

|  |  | Sample 188-1 | | | Sample 460-24 | |
|---|---|---|---|---|---|---|
|  |  | Group A | Group B |  | Group A | Group B |
| adjusted paramters | Tumor: % CD8+ Cells | 15.31 | 13.75 |  | 1.32 | 1.29 |
|  | Non-Tumor: % CD8+ Cells | 14.65 | 16.51 |  | 4.36 | 5.74 |
| blind fit | Tumor: % CD68+ Cells | 27.70 | 23.97 |  | 1.08 | 1.22 |
|  | Non-Tumor: % CD68+ Cells | 10.93 | 11.37 |  | 0.76 | 1.16 |
|  | Tumor: % PD-L1+ Cells | 59.40 | 51.1 |  | 2.55 | 2.29 |
|  | Non-Tumor: % PD-L1+ Cells | 22.97 | 23.36 |  | 1.84 | 2.13 |
|  | Tumor: % Sox10+ Cells | 65.77 | 69.06 |  | 73.67 | 76.78 |
|  | Non-Tumor: % Sox10+ Cells | 2.10 | 1.89 |  | 5.93 | 7.02 |

FIG. 13

APPARATUSES AND METHODS FOR DIGITAL PATHOLOGY

CROSS REFERENCE TO RELATED APPLICATIONS

This patent application claims priority to U.S. Provisional Patent Application No. 62/957,095, filed on Jan. 3, 2020, titled "APPARATUSES AND METHODS FOR DIGITAL PATHOLOGY," herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Biopsy analysis by digital pathology for research, diagnosis and treatment monitoring requires development of instrumentation and methods for histologists, researchers, scientists, clinicians, and/or pathologists to obtain and identify multiple factors present in a single or a plurality of tissue sections on slides.

BACKGROUND

Increases in the number and complexity of tissue biopsy analyses during biomarker discovery research, translational research, and clinical diagnosis and treatment of a range of disorders, including cancer, require faster, more reproducible, and accessible methods to analyze stained tissue samples mounted on slides. Digital pathology is a promising alternative to manual slide analysis, but improvements in image acquisition and analysis methods are needed to provide data (typically in the form of images) that can easily be handled, stored, and importantly, delivered from one data location to another. In particular, it has been particularly difficult to manage the very large amount of data generated by digital pathology, or to facilitate a seamless, high-throughput workflow from staining, to image acquisition, to imagine analysis and interpretation This is particularly true for images that contain high information content, i.e. the position and intensity or 2, 3, or as many as 20 or more different biomarkers such as proteins or nucleic acids.

SUMMARY OF THE DISCLOSURE

Described herein are methods and apparatuses (e.g., devices, systems, etc.) that may be used to optimize and entire histological process flow, from sample preparation and/or staining to image acquisition, image analysis and data management. In particular, these methods and apparatuses may be used to iteratively identify optimal parameters across these different stages of the process so that later stages (e.g., image acquisition and analysis) may be optimized by specifically and efficiently modifying earlier steps. The methods and apparatuses described herein may be used to handle the potentially large and datasets in an efficient (e.g., processor- and memory-efficient) manner. For example, described herein are methods and apparatuses (e.g., systems) for generating image data for a set of stained slides that comprises a tissue sample. This image data may generally include information about one or more (e.g., a plurality) of labels for biomarkers that may be present on cells, cell nuclei and/or cell cytoplasm. This data may include counts of labeled cell and/or labeled regions of cells. The data may include total cell counts, and/or percentages of labeled cells. Any of this data may be specific to one or more regions of tissue.

The present invention relates to methods and software for producing images and generating optimized image data sets, such as, but not limited to Digital Pathology (DP) Whole Slide Images (WSI) that are more readily handled, viewed, optimized, processed, stored, transferred, and analyzed, which can significantly ameliorate problems currently encountered within current DP workflows. The difficulties include but are not limited to: laborious user involvement in the data acquisition software and image (data) analysis software; the absence of coordination between data acquisition and data analysis, leading to inferior images that require significant user manipulation and processing for each and every sample; the software and file incompatibility between different vendors of WSI instrumentation, between different implementations of image processing/analysis tools, and between combinations of the two; the need for a number of highly trained personnel in between the histology lab (where tissue samples are processed and stained), and the researcher's or pathologist's computer where digital images are analyzed (and in some cases paired with medical information, and decisions are made); and the data storage and handling requirements for large sets of image data. The methods described herein may further permit optimization of DP WSI image datasets that are more optimally imaged and analyzed providing for smaller image sets overall, and may thereby offer the potential for more optimized DP images leading to more effective research efforts, diagnoses, and post-intervention monitoring for patients.

For example, a method for generating WSI data for one or more samples is provided, including: selecting a plurality of different imaged regions (or sub-regions) from one or more samples (e.g., "A" sub regions); for each sub-region, selecting a plurality of image acquisition parameters ("B") or variations for each of a plurality C of channels, each channel corresponding to a different marker or plurality of markers; generating $A \times B \times C$ different images; selecting a plurality D of variations of contrast thresholds for each channel, and/or selecting a plurality E variations of thresholds of marker positivity for each channel; generating $A \times B \times C \times D \times E$ number of processed slide images ("masks"); and determining the highest ranking of the processed slide images (masks) of Whole Slide Image data. The highest ranked mask(s) may be used to determine a master (or final) mask.

In general, the methods and apparatuses described herein apply the final mask parameters to the system in order to simplify the otherwise very complex images of the tissue, which may include a large number cells. The use of a final mask that identifies what is and is not cells (and/or regions of cells, such as nucleus, cytoplasm, cell membrane, etc.) as described herein may allow the systems and methods to accurately and quickly analyze even arbitrarily large sets of slides (e.g., tissue samples) and numbers of stains. Applying the masking allows the system and method to directly quantify and determine statistics on the number of cells that are positive for one or more biomarkers, the distribution of biomarkers on groups, or within individual cells, etc. Thus, in general, these methods and apparatuses may provide methods for accurately and quickly (with minimal processing power) identifying a set of final mask parameters that may be used.

In some examples, the method may further include selecting a plurality F of data compression values, wherein generating the second plurality of A×B×C×D×E slide images further includes analyzing the first plurality of A×B×C slide images at each of the plurality F of data compression values, thereby generating a second plurality of slide images, wherein the second plurality comprises an A×B×C×D×E×F number of slide images.

In some examples, ranking may further include reducing a number of the second plurality of slide images to be less than the A×B×C×C×D×E number of slide images, thereby producing an optimized plurality of slide images. In some examples, ranking may be performed automatically.

In some examples, the method may further include selecting a plurality of user selected slide images from the ranked order plurality of slide images.

In some examples, the method may further include selecting a sub-set of imaging and analysis parameters selected from one or more of the plurality B of image acquisition parameters; the plurality C of imaging channels; the plurality D of contrast thresholds; the plurality E of thresholds of marker positivity; and any combination thereof. In some examples, the method may further include selecting a sub-set of the plurality F of data compression values, thereby providing an optimized plurality of data compression values. Selecting the sub-set of the imaging parameters may thereby provide an optimized plurality of imaging and analysis parameters for the one or more samples.

In some examples, each of the plurality A of imaged regions may have an area comprising a selected size. The selected size of each of the plurality A of imaged regions may be selected to be larger than an area of an imaged region failing a statistical sampling test. In some examples, the size of each of the plurality A of imaged regions may include a single Field of View (FOV); a set of adjacent single FOV's; a set of disconnected but closely spaced FOV's, or a set of connected individual FOV's. In some examples, the plurality A of imaged regions may contain some FOV's chosen at random, or all chosen at random. In some examples, multiple FOV's may be chosen from a single slide, while in other variations, at least one FOV is chosen from each different slide. In some examples, the method may further include selecting a different size for the plurality A of imaged regions.

In some examples, the method may further include repeating the image collecting and analysis using the optimized plurality of data compression values F; the optimized plurality of image acquisition parameters B, and/or the different selected size for each of the plurality A of imaged regions, or a different plurality of imaged regions A. In some examples, the optimized plurality of data compression values; the optimized plurality of image acquisition parameters B, and/or the different selected size for each of the plurality A of imaged regions selected for repeating the method may be centered around the best of the plurality of ranked images.

In some examples, selecting the plurality of imaged regions may further include selecting regions comprising sample heterogeneity. In some examples, the selected regions are chosen to appropriately sample an entire section of tissue. In some examples, selecting a plurality of imaged regions comprising a number A of imaged regions may further include randomly selecting the plurality of imaged regions.

In some examples, the plurality B of image acquisition parameters may be from 2 to 10. For fluorescence imaging, the plurality B of image acquisition parameters may include light intensity, and integration time of data acquisition, and for time-resolved measurements, the delay time before detection commences, and/or the width of the excitation pulse, and/or parameters associated with a lock-in amplifier. In some examples, the image acquisition parameters may include the excitation wavelength or wavelengths, or the detection wavelength or wavelengths. In some examples, there may be a window of excitation wavelengths and/or a window of detection wavelengths. In some examples, image acquisition parameters might include the polarization of the incident light and/or the polarization of detected light. In some examples, the image acquisition parameters might include the absence or presence of certain optical elements, (e.g. bandpass or notch filters). In some examples, the image acquisition parameters might include different optical elements chosen for a given imaging channel.

In some examples, the plurality C of imaging channels may be 2 to 40. The imaging methods might include optical methods (e.g. bright field, scattering, fluorescence, phosphorescence, Raman, stimulated Raman, surface enhanced Raman, and others), mass spectrometric methods (e.g. mass cytometry, molecular ion beam imaging), or other methods for image generation (including but not limited to electrical, mechanical, acoustic, and magnetic methods).

In some examples, the plurality D of contrast thresholds may include 4 to 5 thresholds differing by at least 1 order of magnitude. In some examples, the plurality E of thresholds of marker positivity may include 4 to 5 levels differing by at least two orders of magnitude.

In some examples, the plurality F of data compression values may include at least three data compression values which differ from each other by at least a factor of two.

In some examples, the method may further include collecting 2 or more sets of images for each sample of the one or more samples, wherein a first set of images is collected using a universal standardized set of imaging and analysis parameters and a second set of images is collected using the optimized set of imaging and analysis parameters for the one or more samples.

In some examples, the method may further include comparing the first set of images to the second set of images, thereby determining a degree of sameness. In some examples, the method may further include employing the degree of sameness to revise the optimized set of imaging and analysis parameters.

In some examples, the method may further include generating a plurality G of stained slides of the one or more samples, wherein the first plurality of images may include A×B×C×G images and the second plurality of images may include A×B×C×D×E×F×G images. In some examples, the plurality G of stained slides may include 3 to 40 staining parameters.

In some examples, the method may further include associating metadata of each of the one or more samples with the second plurality of slide images. In some examples, the method may further include associating staining parameters used for each of the one or more samples with the second plurality of slide images. In some examples, the method may further include associating a tissue type of each of the one or more samples with the second plurality of slide images.

In some examples, the method may be performed automatically by computer-executable instructions.

In another aspect of the invention, a non-transitory computer-readable medium is provided in which a program is stored for causing a processor to perform a method for generating Whole Slide Image (WSI) data for one or more samples, including: selecting a plurality of A of imaged regions from one or more samples; selecting a plurality B of image acquisition parameters for each of a plurality C of imaging channels; acquiring a plurality of first slide images for each of the one or more samples at each of the plurality B of image acquisition parameters and at each of the plurality C of imaging channels, wherein the first plurality of slide images includes an A×B×C number of images; selecting a plurality D of contrast thresholds; selecting a plurality E of thresholds of marker positivity, generating a second plurality of slide images, by analyzing the first plurality of slide images at each of the plurality D of contrast thresholds and at each of the plurality E of thresholds of marker positivity, where the second plurality of slide images includes an A×B×C×D×E number of slide images; and ranking the third plurality of slide images (in some examples producing a ranked order plurality of Whole Slide Image data). The non-transitory computer-readable medium of claim 1, wherein the method further comprises selecting a plurality F of data compression values, wherein generating the third plurality of slide images further comprises analyzing the first plurality of slide images at each of the plurality F of data compression values, thereby generating the second plurality of slide images, wherein the third plurality comprises an A×B×C×D×E×F number of slide images.

In some examples of the non-transitory computer-readable medium, the method may further include selecting a plurality F of data compression values, wherein generating the second plurality of slide images further includes analyzing the first plurality of slide images at each of the plurality F of data compression values, thereby generating the third plurality of slide images, wherein the second plurality comprises an A×B×C×D×E×F number of slide images.

In some examples of the non-transitory computer-readable medium, ranking may further include reducing a number of the second plurality of slide images to be less than the A×B×C×C×D×E number of slide images, thereby producing an optimized plurality of slide images. In some examples, ranking may be performed automatically.

In some examples of the non-transitory computer-readable medium, the method may further include selecting a plurality of user selected slide images from the ranked plurality of slide images.

In some examples of the non-transitory computer-readable medium, the method may further include selecting a sub-set of imaging and analysis parameters selected from one or more of the plurality B of image acquisition parameters; the plurality C of imaging channels; the plurality D of contrast thresholds; the plurality E of thresholds of marker positivity; and any combination thereof. In some examples, the method may further include selecting a sub-set of the plurality F of data compression values, thereby providing an optimized plurality of data compression values. Selecting the sub-set of the imaging parameters may thereby provide an optimized plurality of imaging and analysis parameters for the one or more samples.

In some examples of the non-transitory computer-readable medium, each of the plurality A of imaged regions may have an area comprising a selected size. The selected size of each of the plurality A of imaged regions may be selected to be larger than an area of an imaged region failing a statistical sampling test. In some examples, the size of each of the plurality A of imaged regions may include a single Field of View (FOV); a set of adjacent single FOV's; a set of disconnected but closely spaced FOV's, or a set of connected individual FOV's. In some examples, the plurality A of imaged regions may contain some FOV's chosen at random, or all chosen at random. In some examples, multiple FOV's may be chosen from a single slide, while in other variations, at least one FOV is chosen from each different slide. In some examples, the method may further include selecting a different size for the plurality A of imaged regions.

In some examples of the non-transitory computer-readable medium, the method may further include repeating the image collecting and analysis using the optimized plurality of data compression values; the optimized plurality of imaging parameters, and/or the different selected size for each of the plurality A of imaged regions. In some examples, the optimized plurality of data compression values; the optimized plurality of imaging parameters, and/or the different selected size for each of the plurality A of imaged regions selected for repeating the method may be centered around the best of the plurality of ranked images.

In some examples of the non-transitory computer-readable medium, selecting the plurality of imaged regions may further include selecting regions comprising sample heterogeneity. In some examples, selecting a plurality of imaged regions comprising a number A of imaged regions may further include randomly selecting the plurality of imaged regions.

In some examples of the non-transitory computer-readable medium, the plurality B of image acquisition parameters may be from 2 to 10. The plurality B of image acquisition parameters may include light intensity and integration time of data acquisition n, and for time-resolved measurements, the delay time before detection commences, and/or the width of the excitation pulse, and/or parameters associated with a lock-in amplifier. In some examples, the image acquisition parameters may include the excitation wavelength or wavelengths, or the detection wavelength or wavelengths. In some examples, there may be a window of excitation wavelengths and/or a window of detection wavelengths. In some examples, image acquisition parameters might include the polarization of the incident light and/or the polarization of detected light. In some examples, the image acquisition parameters might include the absence or presence of certain optical elements, (e.g. bandpass or notch filters). In some examples, the image acquisition parameters might include different optical elements chosen for a given imaging channel In some examples of the non-transitory computer-readable medium, the plurality C of imaging channels may be 2 to 40. The imaging methods might include optical methods (e.g. bright field, scattering, fluorescence, phosphorescence, Raman, stimulated Raman, surface enhanced Raman, and others), mass spectrometric methods (e.g. mass cytometry, molecular ion beam imaging), or other methods for image generation (including but not limited to electrical, mechanical, acoustic, and magnetic methods).

In some examples of the non-transitory computer-readable medium, the plurality D of contrast thresholds may include 4 to 5 ratios differing by at least 1 order of magnitude. In some examples, the plurality E of thresholds of marker positivity may include 4 to 5 levels differing by at least two orders of magnitude.

In some examples of the non-transitory computer-readable medium, the plurality F of data compression values may include at least three data compression values which differ from each other by at least a factor of two.

In some examples of the non-transitory computer-readable medium, the method may further include collecting 2 or more sets of images for each sample of the one or more samples, wherein a first set of images is collected using a universal standardized set of imaging and analysis parameters and a second set of images is collected using the optimized set of imaging and analysis parameters for the one or more samples.

In some examples of the non-transitory computer-readable medium, the method may further include comparing the first set of images to the second set of images, thereby determining a degree of sameness. In some examples, the method may further include employing the degree of sameness to revise the optimized set of imaging and analysis parameters.

In some examples of the non-transitory computer-readable medium, the method may further include generating a plurality G of stained slides of the one or more samples, wherein the first plurality of images may include A×B×C×G images and the second plurality of images may include A×B×C×D×E×F×G images. In some examples, the plurality G of stained slides may include 3 to 40 staining parameters.

In some examples of the non-transitory computer-readable medium, the method may further include associating metadata of each of the one or more samples with the second plurality of slide images. In some examples, the method may further include associating staining parameters used for each of the one or more samples with the second plurality of slide images. In some examples, the method may further include associating a tissue type of each of the one or more samples with the second plurality of slide images.

For example, described herein are method (such as methods for generating image data for a set of stained slides that comprises a tissue sample) that include: selecting a plurality of sub-regions from one of the stained slides; identifying, for each imaging channel of a first plurality of imaging channels, either a first number of variations of contrast thresholds, a first number of variations of thresholds of marker positivity, or a first number of variations of contrast thresholds and a first number of variations of thresholds of marker positivity; generating a plurality of masks for each of the plurality of sub-regions corresponding to each combination of the variations of contrast thresholds and variations of thresholds of marker positivity for each imaging channel of the first plurality of imaging channels, wherein each mask is segmented to identify cells; ranking the plurality of masks (to determine the highest ranking mask(s)); selecting a set of final mask parameters from the plurality of masks based on the rankings; and generating a set of slide images for all slides of the set of stained slides using the set of final mask parameters.

For example, a method for generating image data for a set of stained slides that comprises a tissue sample may include: selecting a plurality of sub-regions from one of the stained slides, wherein at least one of the sub-regions includes a structure that is substantially free of cells; identifying, for each imaging channel of a first plurality of imaging channels: a first number of variations of contrast thresholds, a first number of variations of thresholds of marker positivity, or a first number of variations of contrast thresholds and a first number of variations of thresholds of marker positivity; generating a plurality of masks comprising a mask for each of the plurality of sub-regions corresponding to each combination of the variations of contrast thresholds and the variations of thresholds of marker positivity for each imaging channel of the first plurality of imaging channels, wherein each mask is segmented to identify cells using the variations of contrast thresholds and the variations of thresholds of marker positivity; ranking the plurality of masks (e.g., to determine the highest ranking mask(s)); selecting a set of final mask parameters from the plurality of masks based on the rankings; and generating a set of slide images for all slides of the set of stained slides using the set of final mask parameters.

In general, ranking may include determining which masks have a higher score than others. Ranking does not require determining an absolute scoring or ranking; the method, and particularly the automated method, may determine the highest ranked mask(s) without having to determine relative rankings for lower ranked masks.

Any of these methods may include applying the final mask parameters to the entirety of the stained slides in the set of stained slides (generating a final mask for each slide), so that all of the cells that can be identified are identified and the resulting final slides may be analyzed to determine a count and/or distribution of cells labeled with one or more (or each) of the markers for each channel or combinations of channels.

Selecting the plurality of sub-regions from one of the stained slides may include selecting the sub-regions so that at least one of the sub-regions includes a structure that is substantially free of cells. In some examples, identifying may include identifying a number of variations of image acquisition parameters for each imaging channel of a first plurality of imaging channels.

Any of these methods may include selecting a plurality of data compression values, as described above.

All or some of the steps performed as part of the method (and/or by a system) may be performed by a trained network, such as an artificial intelligence agent that is trained using a curated dataset. For example, the step of ranking may be performed by a trained network. In some examples the step(s) of selecting variations of contrast thresholds, and/or variations of thresholds of marker positivity may be performed by a trained network.

Any of these methods may also include iterating the steps of identifying and generating for different imaging channels. For example, the final mask parameters may be refined by using additional imaging channels. In some examples the at least one of the imaging channels may specify a nuclear stain, such as DAPI, in addition to one or more other stains, which may be nuclear stains, membrane-specific stains, cytoplasm stains, or any combination of these.

As mentioned above, the methods and apparatuses described herein may include determining, from the set of stained slides, statistics on the labeled cells, using the masks to confirm the locations for cells. Any or all (or combinations of) the channels and their corresponding biomarkers, may be analyzed using the final mask parameters determined as described herein. For example, the methods and systems may determine statistics on labeled cells for a second plurality of imaging channels that is larger than the first plurality of imaging channels.

In some examples, selecting the plurality of sub-regions from one of the stained slides may include selecting a different size for each of the sub-regions. In general, the different sub-regions may be selected so that at least one sparse region (e.g., a region including a structure that is relatively free of cells) and/or a relatively crowded region (e.g., a region including clusters of cells) may be selected. As used herein, "relatively free of cells" may refer to a region in which the original slide shows little or no (e.g., less than 10%, less than 8%, less than 7%, less than 5%, less than 4%, less than 3%, less than 2%, less than 1%, etc.) staining within a contiguous area. These areas that are relatively free of cells may be structures that do not include cells such as vessels, lumen, region of ECM, etc.).

Any of these methods may include forming the mask by segmenting each sub-region using the sets of parameters (e.g., the variations of contrast thresholds, variations of thresholds of marker positivity, etc. for each channel) for each sub-region. For example, the methods and systems described herein may include segmenting each mask to identify cells using the variations of contrast thresholds and the variations of thresholds of marker positivity.

As mentioned, any of the methods described herein may be performed by a system configured to perform the method. Any of these systems may include software, hardware and/or firmware for performing the steps. A system may be self-contained, e.g., receiving inputs from the user. The system may be, for example, a system for generating image data for a set of stained slides that comprises a tissue sample. For example, a system may include: one or more processors; memory coupled to the one or more processors, the memory configured to store computer-program instructions, that, when executed by the one or more processors, perform a computer-implemented method comprising: selecting a plurality of sub-regions from one of the stained slides; identifying, for each imaging channel of a first plurality of imaging channels, either a first number of variations of contrast thresholds, a first number of variations of thresholds of marker positivity, or a first number of variations of contrast thresholds and a first number of variations of thresholds of marker positivity; generating a plurality of masks for each of the plurality of sub-regions corresponding to each combination of the variations of contrast thresholds and variations of thresholds of marker positivity for each imaging channel of the first plurality of imaging channels, wherein each mask is segmented to identify cells; ranking each of the plurality of masks; selecting a set of final mask parameters from the plurality of masks based on a rank order of the rankings; and generating a set of slide images for all slides of the set of stained slides using the set of final mask parameters. Any of the method steps described above may be performed by the system. For example, the memory may include instructions that, when executed by the one or more processors, may include selecting the plurality of sub-regions from one of the stained slides by selecting each of the sub-regions so that each sub-region includes a structure that is substantially free of cells.

In some examples the memory may include instructions that, when executed by the one or more processors identify a number of variations of image acquisition parameters for each imaging channel of a first plurality of imaging channels, and/or select a plurality of data compression values.

Any of these systems described herein may include one or more trained networks, as described herein. For example the trained network may include a trained network for scoring the subset of the region identified

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the claims that follow. A better understanding of the features and advantages of the present invention will be obtained by reference to the following detailed description that sets forth illustrative examples, in which the principles of the invention are utilized, and the accompanying drawings of which:

FIGS. 10A-10C shows a comparison between the first sub-region of the slide (as shown in FIG. 7A) and a pair of masks generated as described herein. FIG. 10A shows the original image of two channels of the first sub-region. FIG. 10B shows a first mask generated with a first set of parameters, while FIG. 10C shows a second mask, generated with a second set of parameters. Scoring of these masks (e.g., automated and/or semi-manual) shows the mask of FIG. 10B more accurately identified cells (see circled regions) as compared to the mask of FIG. 10C.

FIGS. 11A-11C shows a comparison between the second sub-region of the slide (as shown in FIGS. 8A and 9A) and a pair of masks generated as described herein. FIG. 11A shows the original image of two channels of the first sub-region. FIG. 11B shows a first mask generated with a first set of parameters, while FIG. 11C shows a second mask, generated with a different set of parameters. Scoring of these masks (e.g., automated and/or semi-manual) shows the mask of FIG. 11B more accurately identified cells (see circled regions) as compared to the mask of FIG. 11C.

FIG. 12 shows table 1, summarizing the ranking of different masks generated as described herein.

FIG. 13 shows table 2, comparing a traditional method for determining imaging/masking parameters used for analysis with the results of an example analyzed as described herein.

DETAILED DESCRIPTION

The study of tissue biopsy materials has enabled progress in discovery and translational research, diagnosis, patient stratification and post-surgical evaluation of patient tissue samples. However, the traditional process for evaluation has often required one or more of: limiting a biomarker to a single species; manually observing the slide individually through a light microscope; and relying upon qualitative assessment of the biomarker, rather than quantitative measurements.

"Contrast threshold" as used herein refers to a ratio of signal to noise (S/N) in the observed image, at low signal levels, noise resulting from the statistical nature of fluorescence detection reduces the number of grey levels that can be discriminated in an image.

Figure 1:
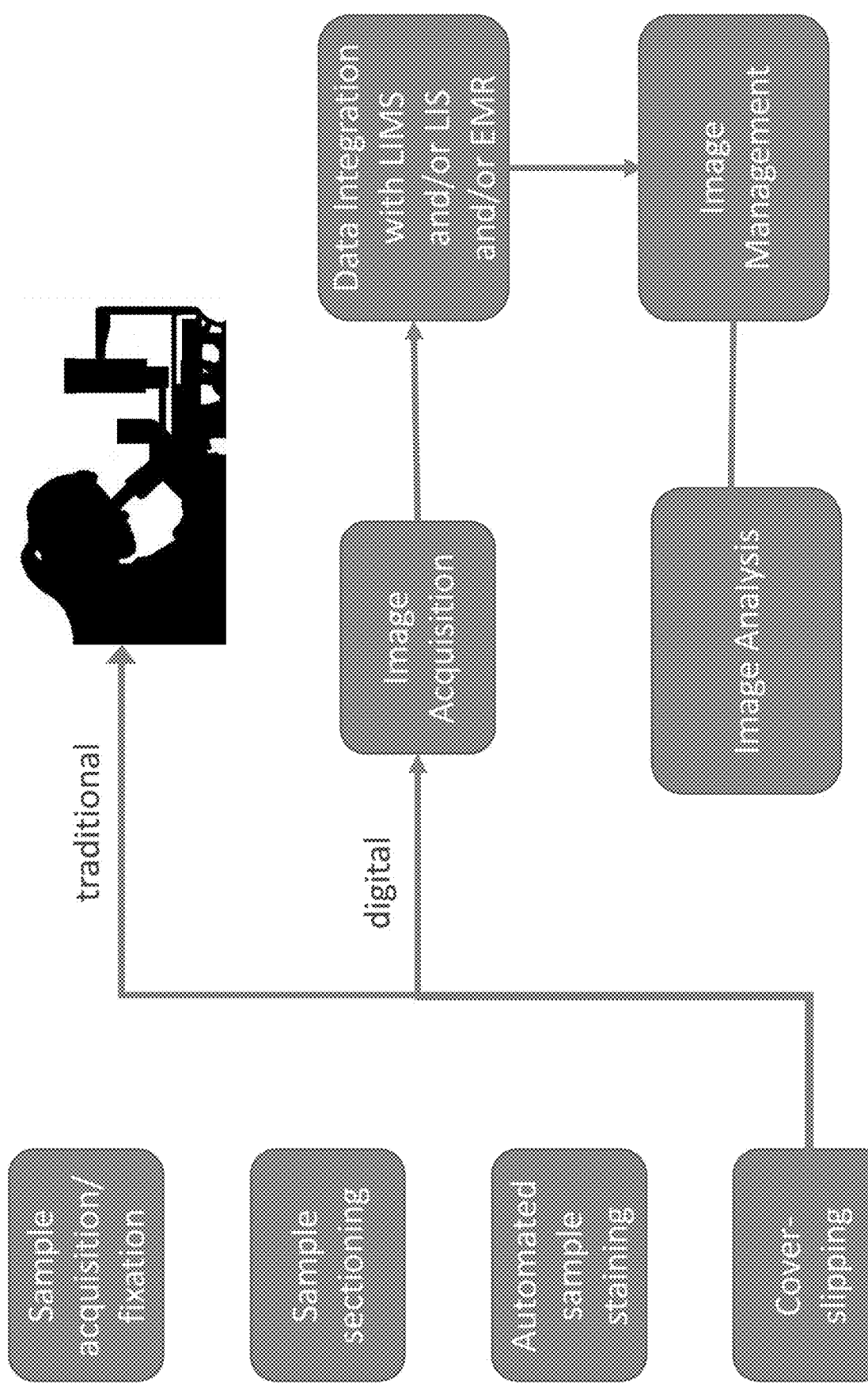
FIG. 1 is a schematic representation comparing traditional analysis of a biopsy slide with digital pathology data management.

In FIG. 1, a comparison between traditional pathology image analysis and digital pathology image analysis is shown. While preparative aspects of the process can now be automated and be controlled by a LIMS (Laboratory Information Management System), the increased numbers of biopsy slides now generated still hit the same limitations when using traditional pathology. Additionally, in current research and diagnostic procedures alike, multiplex stainings (i.e. the detection of multiple markers on a single tissue sample greatly adds to the process complexity.

In contrast, using digital pathology, automating image acquisition, digitization, data integration, and data management, provides the end user with a richer set of data to interrogate, enabling better and faster decision-making. Freeing the end user from laborious image acquisition and image processing steps, while concentrating efforts upon use of his/her judgement also leads to higher efficiencies and lower costs. Advances in high-speed bright field and fluorescence imaging, automation for sample processing and image acquisition, and advances in networking, cloud and IT infrastructure are making DP a competitive technology over traditional histopathology.

DP begins with a tissue slide stained with reagents and labels. Typically the tissue sample is a thin section either formalin-fixed and paraffin embedded (so-called FFPE samples), or frozen in a fresh state (so-called fresh frozen). Most tissue samples are typically sectioned to a thickness of 4-6 microns, but in some cases, sections are 20 microns, and in other applications, thicker tissues (such as whole embryos) are used. A wide variety of stainings may be used and may be directed to different types of detection. Labels detectable under bright field imaging include commonly used chromogenic stains such as hematoxylin and eosin stain (H & E). Hematoxylin reacts with negatively charged cell components such as nucleic acids in the nucleus, staining blue, while eosin reacts with positively charged species, staining proteins nonspecifically within the cytoplasm. Immunohistochemical staining (IHC) may also be performed with chromogenic reagents detected in bright field. IHC may be antibody based or have other specific binding features permitting specific and selective binding. HIS often is performed using fluorescently labeled reagents such as antibody, and detection may be performed across a wide spectrum of fluorescence, e.g., from about 350 nm to about 900 nm. Newer fluorescence labels and detection apparatus can extend the detection window into the near- or even mid-IR, i.e. out to 1500 nm. Alternatively, IHC may be performed with reagents where labelling may include labels containing elemental mass tags, such as isotopically pure lanthanide labelled antibody reagents, by mass spectrometry (MSIHC). Multiplex MSIHC can be performed without cross-interference. Other types of labels include but are not limited to Raman labels, particle-based labels, magnetic labels, acoustic labels, isotopic labels such as deuterium (for hydrogen), and IR vibrational labels. Some of these labels may be exogenous (i.e. added to the sample), while others may be endogenous (i.e. naturally occurring in the sample).

The slides may be counterstained to provide orientation. In some examples, the slides may be coverslipped.

A whole slide image (WSI) is typically acquired on a software-controlled whole side scanner typically a scanning microscope using a 2×, 5×, 10×, 20×, or 40× air objective, or an oil immersion or water immersion objective, comprising some number of fields of view (FOV), e.g. from 2-10,00 or more. The FOV are stitched together to form the WSI. For each biomarker/reagent/label combination (i.e. each channel), there is a separate WSI. For example, in a 5-plex fluorescence assay such as those offered commercially by Ultivue, Roche, CellIDx and others, the 5 channels can include DAPI (nuclear stain), FITC, TRITC, Cy 5, and Cy 7, each of the latter four corresponding to a different protein marker labelled with (four) differently-emitting fluorophores. The ensuing 5 WSI are merged together to form a single multiplex image. However, the images required to get this information become more massive, depending on the level of detail needed. For example, a typical WSI for protein staining may be from about 1 GB to about 100 GB, while a typical WSI for nucleic acids staining may be from about 1 GB to about 1 Tb or even larger.

Figure 2A:
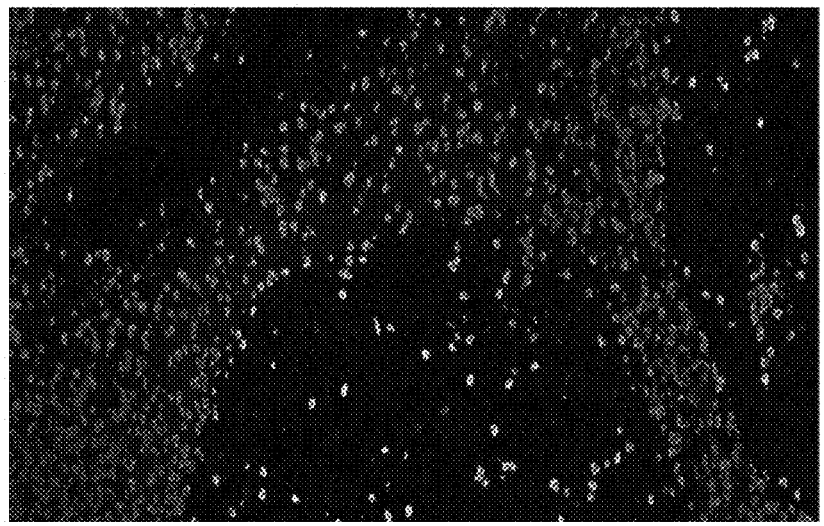
FIGS. 2A to 2D are photographic representations of a region of interest of an imaged slide showing differing channels of fluorescent antibody staining.
Figure 2B:
Figure 2C:
Figure 2D:
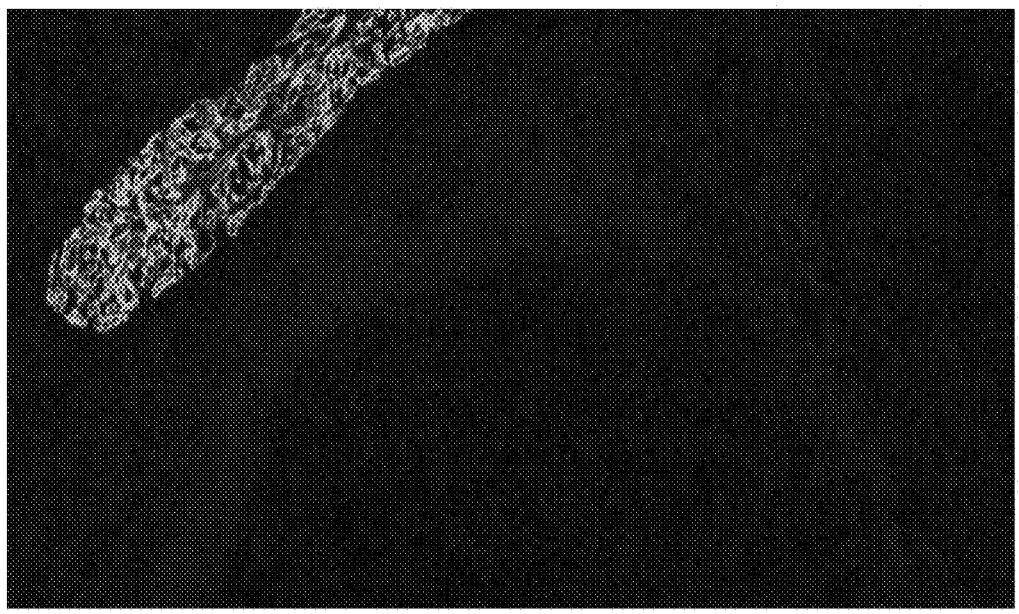
Figure 2E:
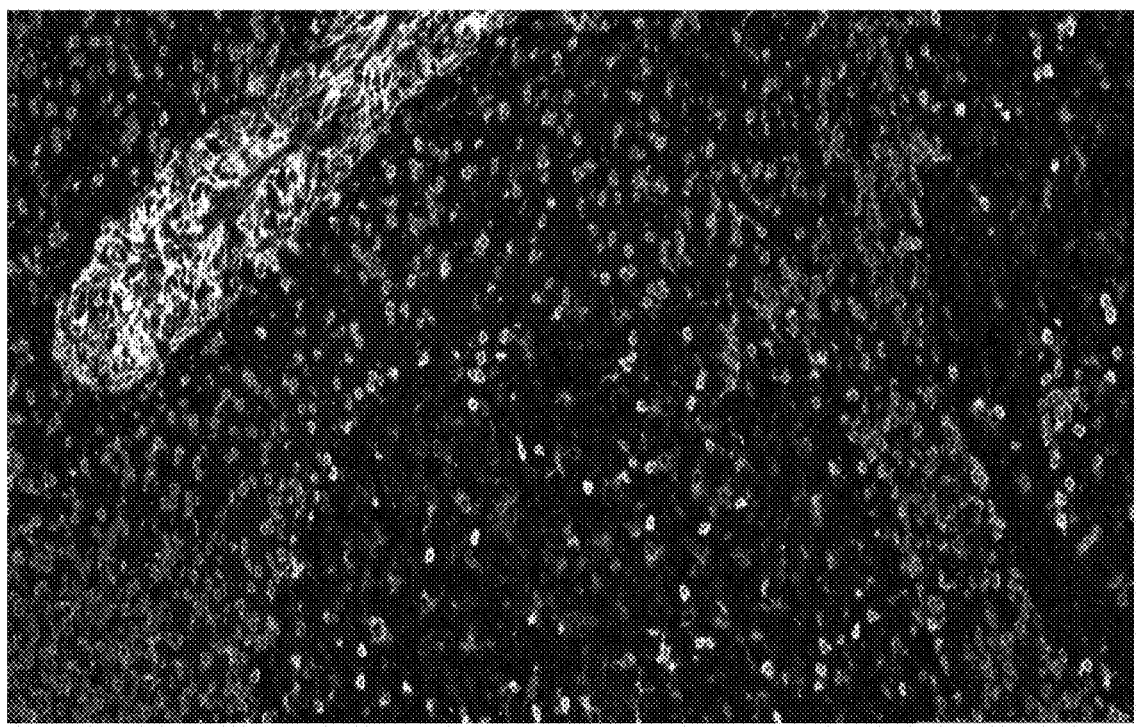
FIG. 2E is a photographic representation of FIGS. 2A-2D showing the four channels of staining in a composite image.

The critical information obtained from any of these staining methodologies is the spatial relationship or context of the variously labeled entities. An example is shown in FIGS. 2A to 2D, showing a WSI having four stains. FIG. 2A shows anti-CD8 labelling in yellow, with nuclei stained dark blue (DAPI) marking the presence of a cytotoxic T lymphocyte. FIG. 2B shows anti-CD68 labelling in green, and DAPI stained nuclei, marking the presence of CD68+ macrophages. FIG. 2C shows the presence of programmed death ligand-1 (PD-L1) expression in red and nuclei stained by DAPI. FIG. 2D shows cytokeratin in light blue, which marks motile cells and may indicate cancer progression. The association in space, e.g. the context, between PD-L1 expression and cytokeratin expression, which may indicate apoptosis along with the presence of macrophages and cytotoxic T cells is important to understand potential therapeutic approaches in various cancers. The level of detail also indicates the requirement for very large images.

A key step in currently available protocols for fluorescently labeled samples is for the user to manually set light intensities, irradiation times, and integration times for each of the five channels for image acquisition. Depending on the type of optical detection system used, many other parameters could also be varied. For work encompassing more than one tissue sample, it may be desirable to have a single set of identical acquisition parameters for each sample. In other variations, it may be desirable to adjust the parameters uniquely for subsets of samples or even for each individual sample. The image is then uploaded into image analysis software (free or commercial).

Figure 3A:
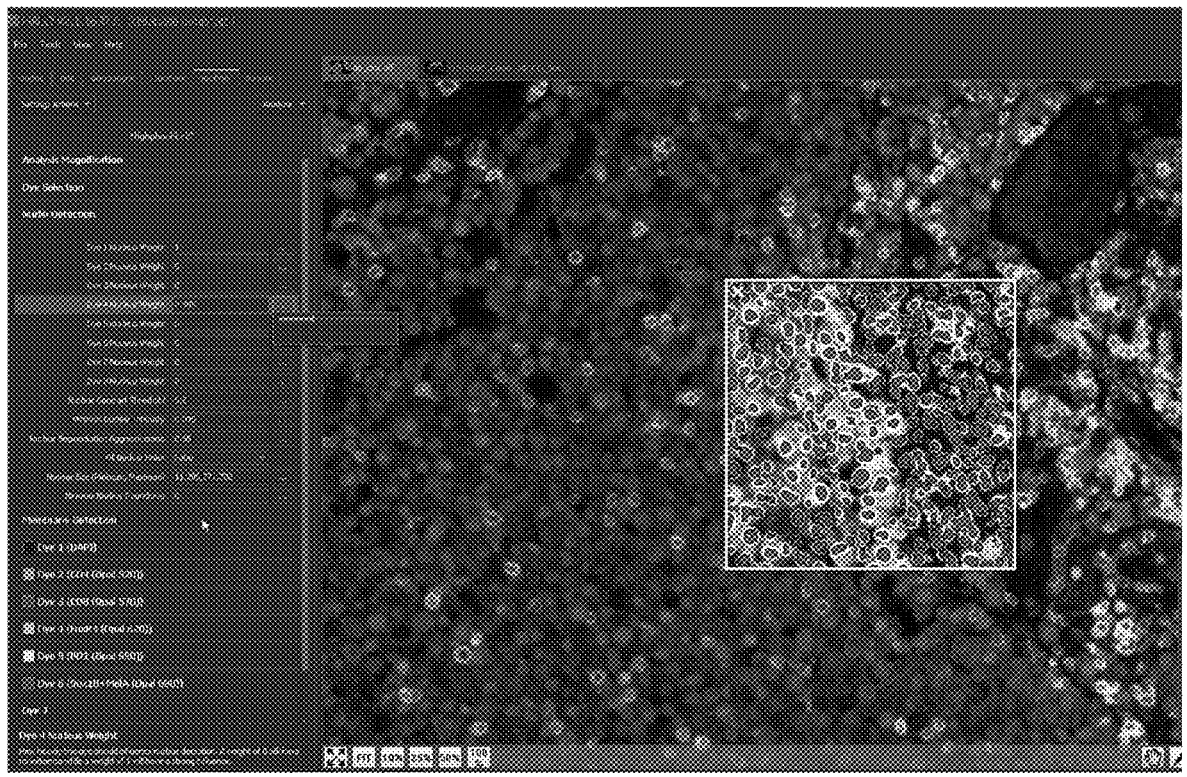
FIGS. 3A to 3G are photographic representations of a currently available slide analysis user interface.
Figure 3B:
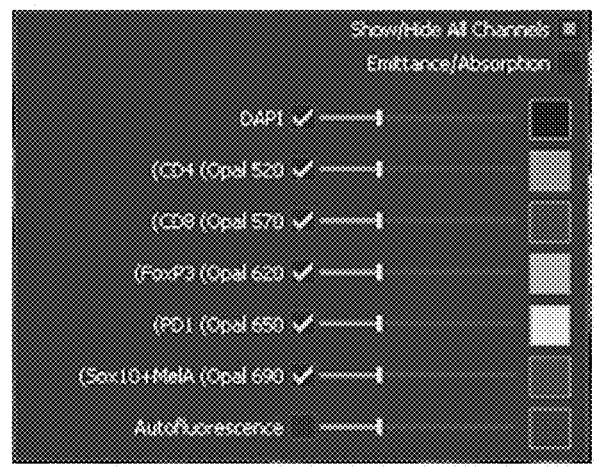
Figure 3C:
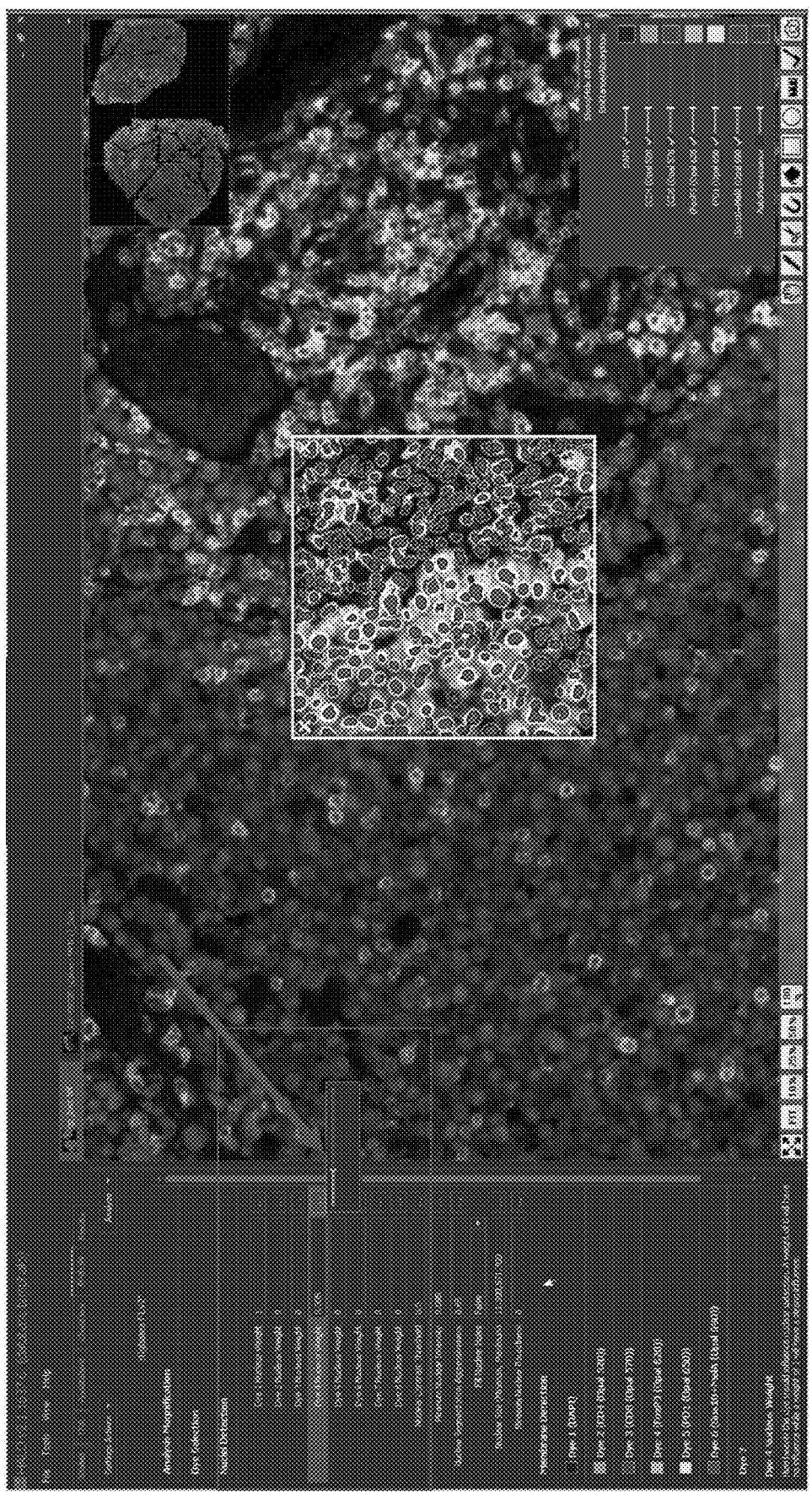
Figure 3D:
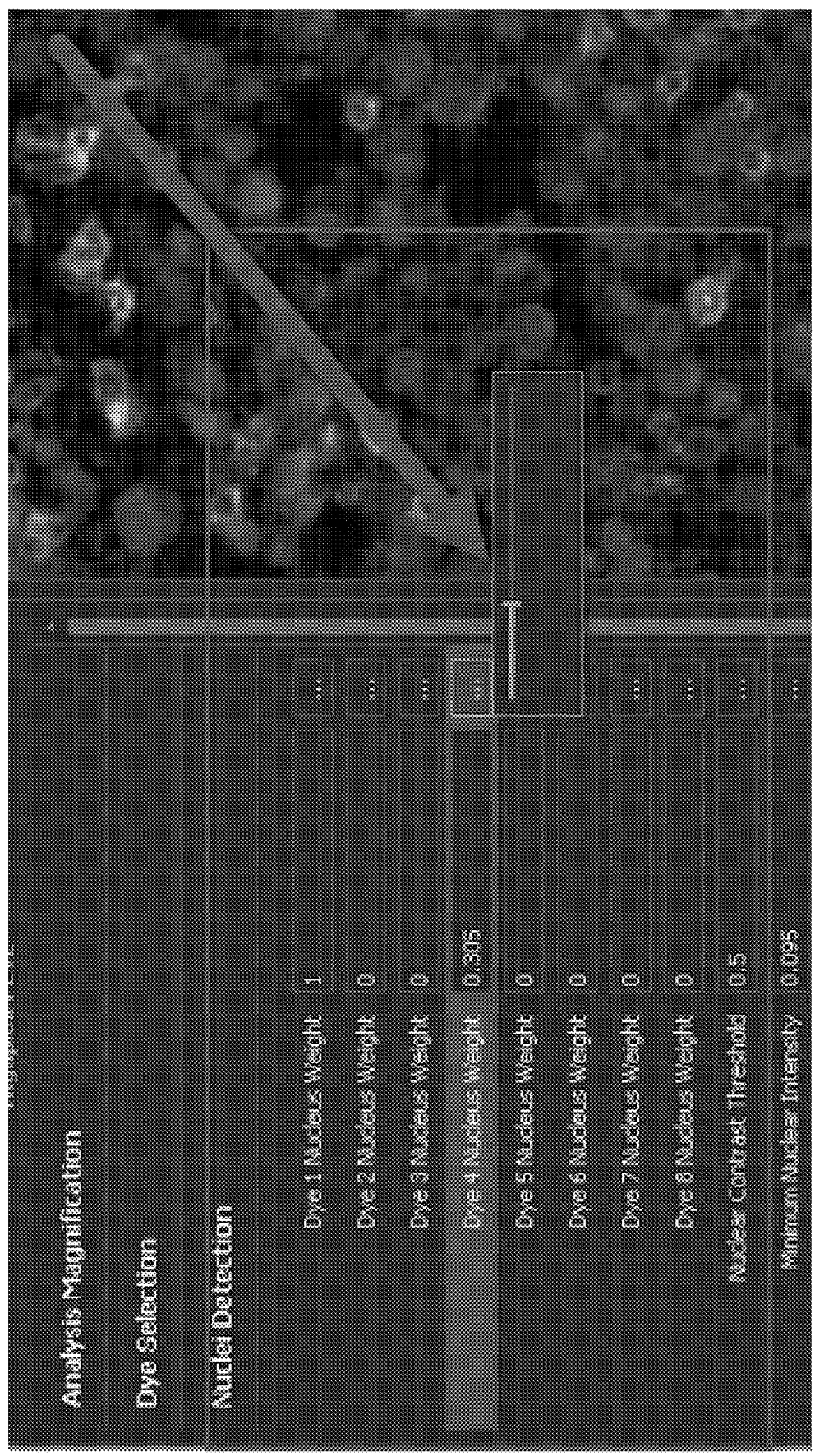
Figure 3E:
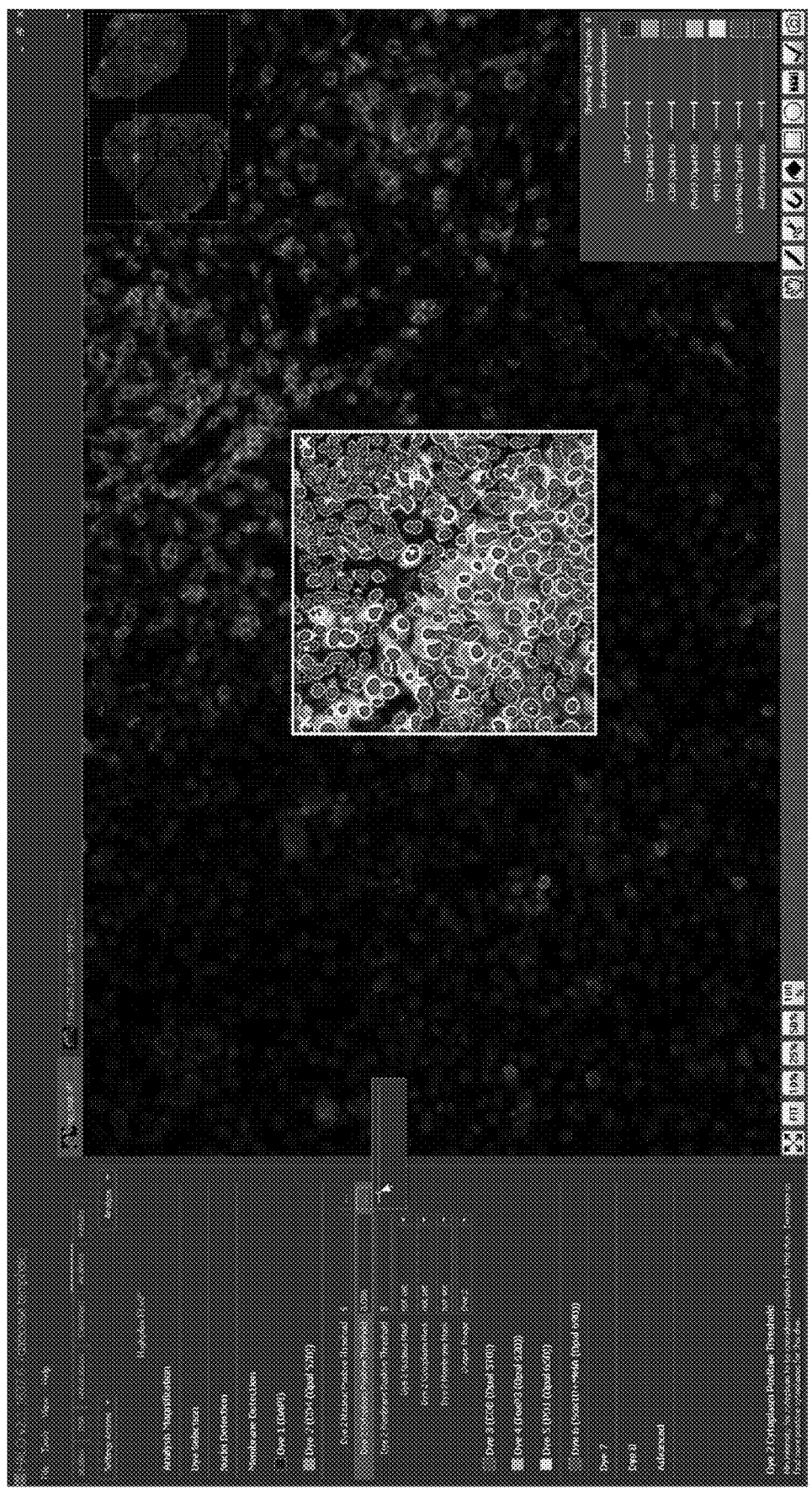
Figure 3F:
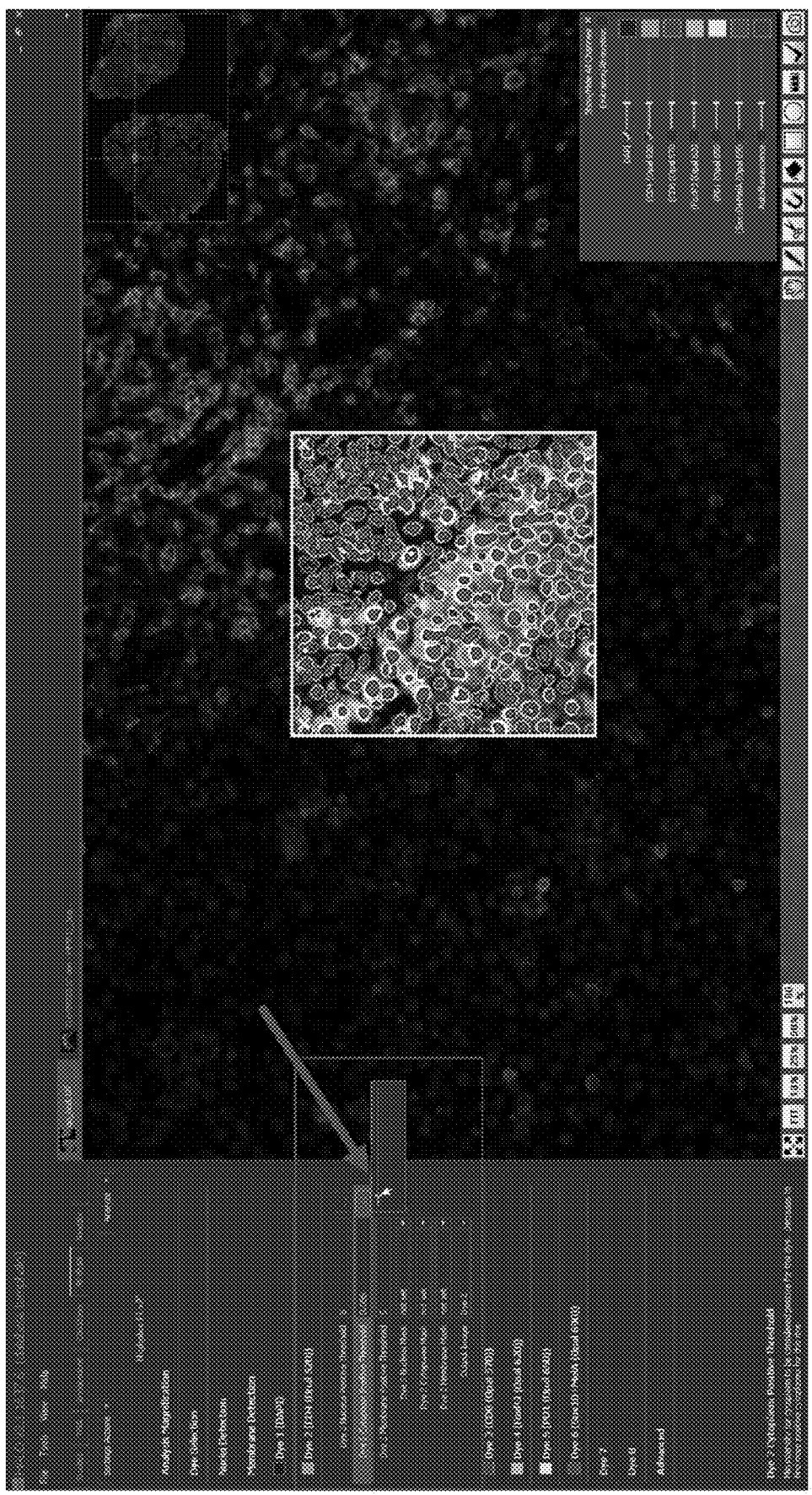
Figure 3G:
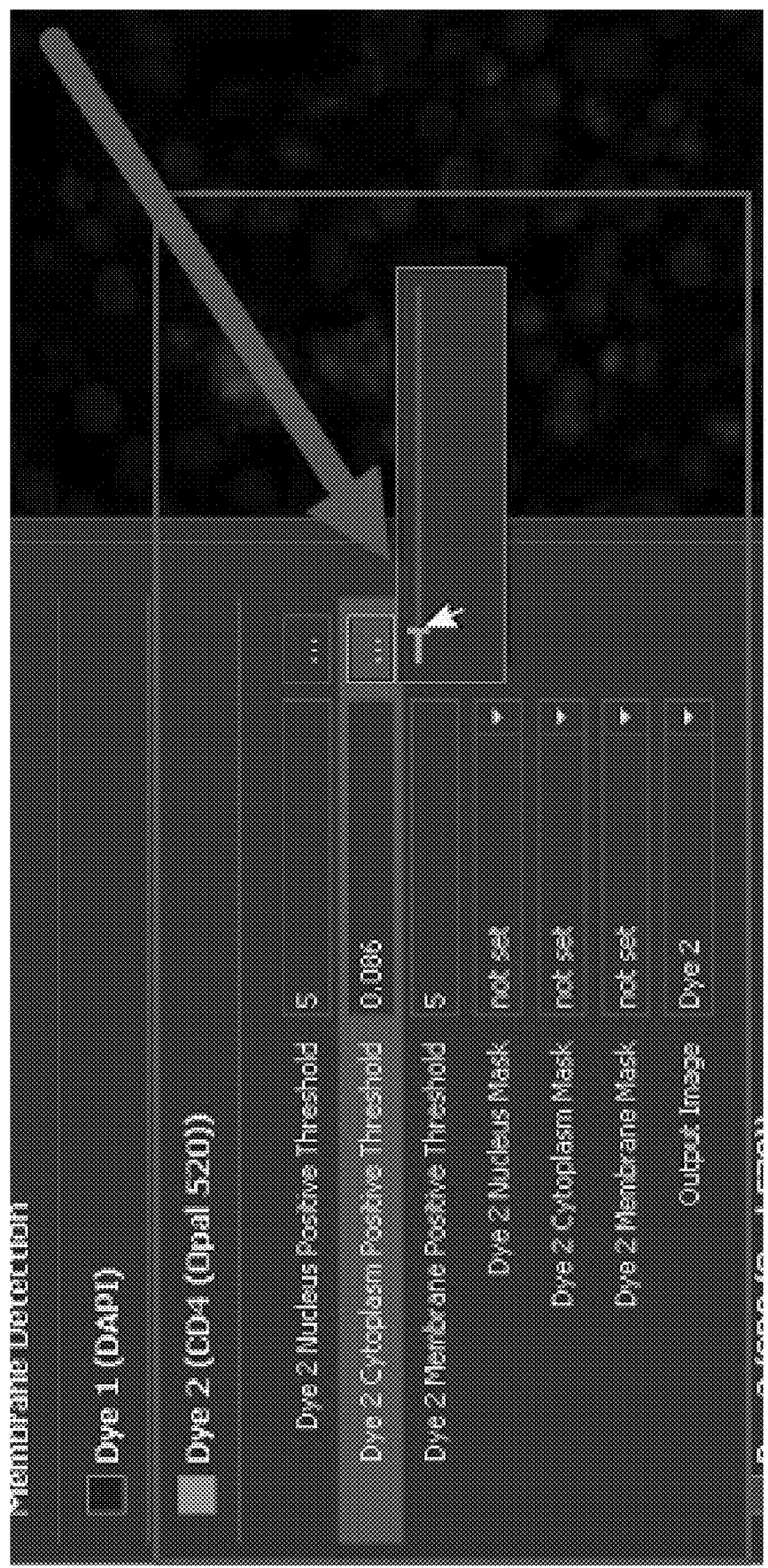

Currently, the user must manually set or adjust the threshold for what is signal and what is noise, as shown in FIGS. 3A-3G. FIGS. 3A and 3C-3G illustrate masks used to identify cells within the stained slides. In FIG. 3A, a region is highlighted to demonstrate the multiple user inputs needed to decide on the saturation of a first dye (DAPI) used to stain nuclei. At the left side of the image is the user input menu showing a plurality of saturation levels for Dye 1, assigned to be DAPI. The original assignment can be seen in FIG. 3B where Dye 1 has been assigned as DAPI, and a blue presentation color assigned to Dye 1. Weighting the dye saturation in order to obtain optimal segregation of nuclei from other objects is made by iterative assignments of the saturation of all the dyes assigned to the image, as shown in FIGS. 3C and 3D, where the arrow points to the various inputs available for adjustment by the user. FIG. 3D shows an enlarged portion of FIG. 3C, and illustrates the subjective inputs needed. The results are judged by the user and may need to be reiteratively manipulated. FIG. 3E shows the initial process for assigning the next dye, Dye 2, which marks membrane proteins (e.g., CD4) labeled by dye Opal 520, and assigned a green presentation color. As shown in more detail in FIGS. 3F and 3G, a number of thresholds and masks need to be assigned individually by the user to arrive at the image properties that are optimal for the user's purposes. As seen specifically in FIGS. 3D and 3G, a number of these settings must be performed using a slider-type interface, which is not particularly controllable nor reproducible. This process is continued for each of the stains used. As shown in FIGS. 3A-3G, assignment and weighting must be performed for CD8 (Opal 570 label, assigned bright red; FoxP3 (Opal 620 label), assigned light blue; Sox10+ MelA (Opal 690) assigned dark crimson, and autofluorescence, assigned dark green. The user has manually set or adjusted threshold levels for each marker, e.g., what is the cutoff for intensities between cells that are positive for a given marker and those that are negative. Once instructed, the software identifies individual cells within the tissue sample. The software then counts up the amount of positive and negative cells for each marker across the entire sample, which depending on the tissue type and dimensions, could include as few as tens of cells, or as many as 10,000,000 or more. e. Once the number of positive cells for each marker have been calculated, additional elements of the analysis software enable phenotypic mapping (e.g. how many of each type of cell, as defined by positivity/negativity for particular marker(s), are present, cell proximity calculations (how many of a particular type of cell are in proximity to another type), and other potentially useful parameters. This is a laborious process. Adoption of this technology has accordingly been slow.

Figure 4:
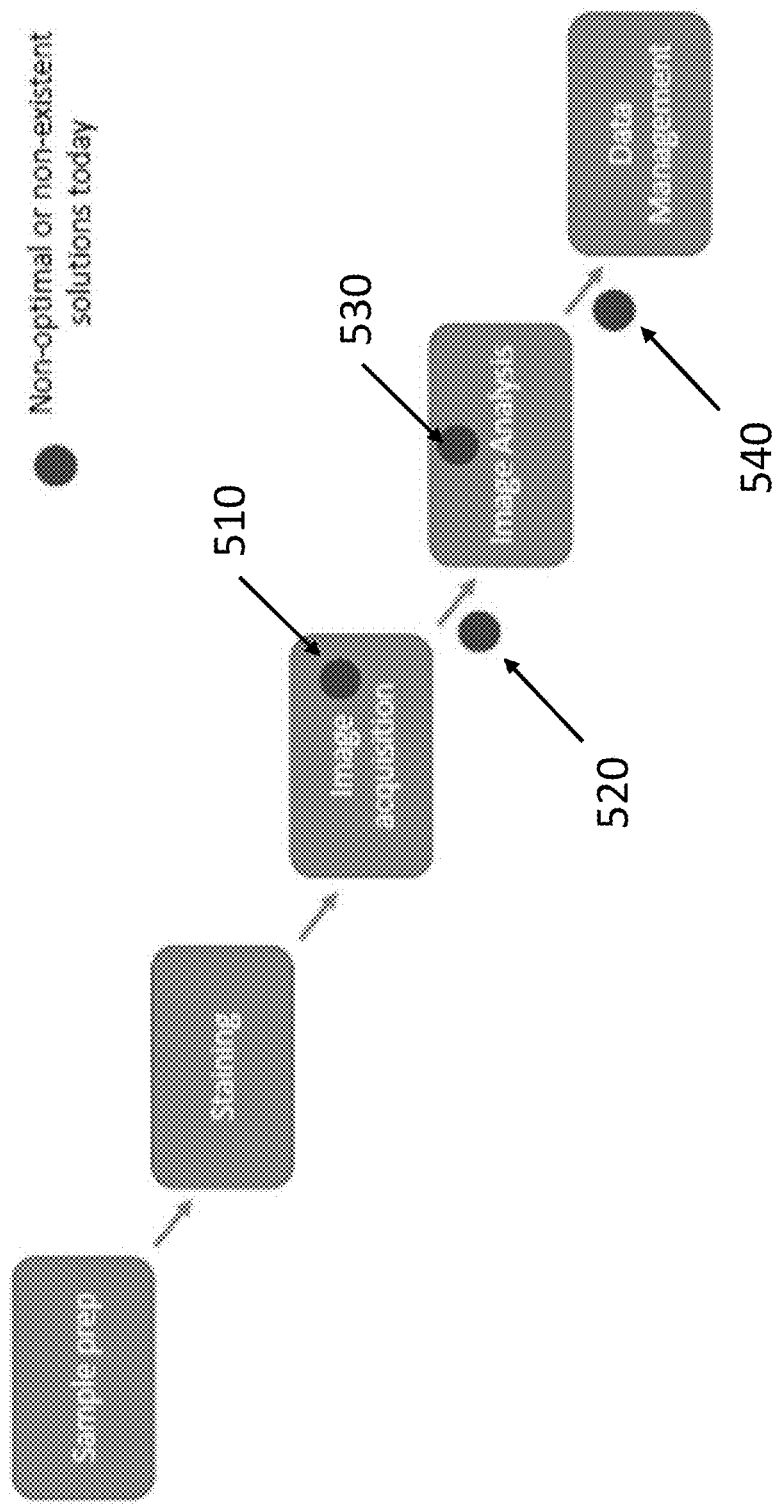
FIG. 4 is a schematic representation of a method of digital pathology, indicating parts of the process where additional software development has been described herein.

As shown in FIG. 4, there are significant points within the DP process that currently have sub-optimal or no solution at all to process impediments. A first major problem to be solved in digital pathology for analysis for multiplexed assays is laborious user involvement in the data acquisition software 510 and data analysis software 530.

Another major problem to be solved in digital pathology for analysis for multiplexed assays is the absence of coordination between data acquisition and data analysis, leading to inferior images that require significant user manipulation. In one non-limiting example, 'multi-channel' imaging methods requires registration of the multiplexed images; physical displacements can easily occur during sequential imaging of the same specimen.

A third major problem to be solved in digital pathology for analysis for multiplexed assays is the software and file incompatibility 520 between different vendors of WSI instrumentation, between different implementations of image analysis tools, and between combinations of the two. Closely related to this problem is the incompatibility between different types of data from similar or identical samples. For example, it would be desirable to visualize H&E and/or IHC and/or FISH and/or mass cytometry and/or infrared and/or Raman and/or other types of image data acquired on a single tissue, or on serial sections, in a single image.

A fourth major problem to be solved in digital pathology for analysis for multiplexed assays is the need for a number of highly trained personnel in between the histology lab (where tissue samples are processed and stained), and the pathologist's office (where digital images are analyzed, paired with medical information, and decisions are made).

A fifth major problem to be solved is the data storage and handling requirements (data management 540) for such large blocks of imaging data that need to be kept correlated and accessible for the pathologist and associated collaborators. The set of images which may need to be transferred between organizations and various medical databases needs to be reduced in size to data packages capable of being stored in the cloud or transferred to other organizations without excessive demand.

Together, these problems make it difficult to carry out digital pathology on multiplex-stained tissue samples at high-throughput. Applicant has discovered methods for producing images and generating optimized image datasets containing the DP WSI which are more readily handled, viewed, stored and transferred, which can significantly ameliorate these problems and may offer the potential for more optimized DP images leading to more effective research efforts, diagnoses, and post-intervention monitoring for patients.

Figure 5:
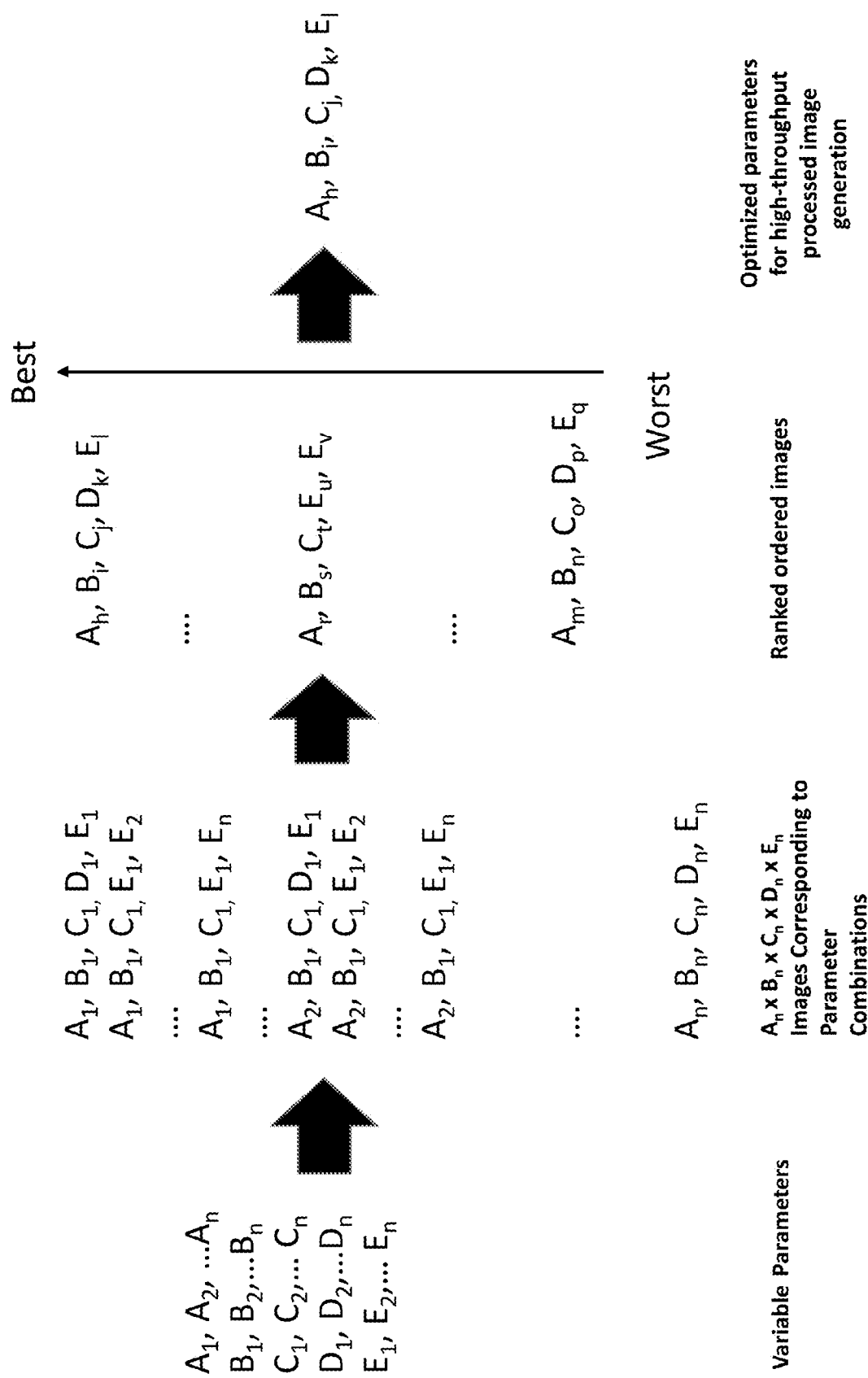
FIG. 5 is a schematic representation of a method for producing images and generating optimized image data sets containing Digital Pathology (DP) Whole Slide Images (WSI) according to some examples of the disclosure.

Method for Generating Whole Slide Image. As illustrated in FIG. 5, a method for generating Whole Slide Image (WSI) data for one or more samples is provided, including selecting a plurality of imaged regions comprising a number, A, of imaged regions within each of the one or more slides and selecting a plurality, B, of image acquisition parameters for each of a plurality, C, of imaging channels. The method includes generating a plurality of first slide images for each of the one or more samples comprising an A×B×C number of images. Generating the plurality of first slide images for each of the one or more samples may further include acquiring an image at each of the plurality, B, of image acquisition parameters and at each of the plurality, C, of imaging channel, providing the A×B×C number of images in the plurality of first slide images. The method includes selecting a plurality, D, of contrast thresholds; selecting a plurality, E, of thresholds of marker positivity; and generating a second plurality of slide images comprising an A×B×C×D×E number of slide images. The plurality, D, of contrast thresholds may include at least one contrast threshold having a value differing by one or more orders of magnitude from contrast thresholds of a remainder of the plurality, D, of contrast thresholds. The plurality D of contrast thresholds may range from about 1 order of magnitude difference, 2, orders of magnitude difference, three orders of magnitude difference, or more. Generating the second plurality of slide images may include analyzing the first plurality of slide images at each of the plurality, D, of contrast thresholds and at each of the plurality, E, of thresholds of marker positivity. The method includes ranking each of the second plurality of slide images, thereby producing a ranked order plurality of Whole Slide Image (WSI) data.

There may be a number A of imaged regions from about 1, 10, 100, 200, 500, 750, 1000 or more. a set of disconnected but closely spaced FOV's, or a set of connected individual FOV's. In some examples, the plurality A of imaged regions may contain some FOV's chosen at random, or all chosen at random. In some examples, multiple FOV's may be chosen from a single slide, while in other variations, at least one FOV is chosen from each different slide. The number A of imaged regions may be less than or the same as the number of FOV in the WSI, which may be from about 5 to about 10,000. An initial decision for which regions to include may be based on the actual tissue sample as the sample may not fill the entire imaginable area of the slide.

Removal of some regions of the slide may prevent wasting imaging time on a non-useful region. In some examples, selecting the plurality of imaged regions may include selecting regions to encompass predicted or observed sample heterogeneity, e.g., selecting dissimilar areas. This selection may be based on a wide-angle view to represent the sample heterogeneity. In some examples, the selected regions are chosen to appropriately sample an entire section of tissue. In some examples, selecting the plurality of imaged regions having a number A of imaged regions is performed randomly. In determining the optimized imaging parameters, the size of each of the plurality A of imaged regions may be optimized as well. A selected size of each of the plurality A of imaged regions may be selected to be larger than an area of an imaged region failing a sampling test. For example, a lower threshold of imaginable pixels within the imaged region may be set. Other tests may be used to set an area of the plurality A of imaged regions, such as any statistical sample test. In some examples, optimizing the plurality A of imaged regions may include selecting a size for the plurality A of imaged regions that is different from the size used in the initial image collection.

In some examples, the plurality B of image acquisition parameters may be from 2 to 10. For fluorescence imaging, the plurality B of image acquisition parameters may include light intensity, and integration time of data acquisition, and for time-resolved measurements, the delay time before detection commences, and/or the width of the excitation pulse, and/or parameters associated with a lock-in amplifier. In some examples, the image acquisition parameters may include the excitation wavelength or wavelengths, or the detection wavelength or wavelengths. In some examples, there may be a window of excitation wavelengths and/or a window of detection wavelengths. In some examples, image acquisition parameters might include the polarization of the incident light and/or the polarization of detected light. In some examples, the image acquisition parameters might include the absence or presence of certain optical elements, (e.g. bandpass or notch filters). In some examples, the image acquisition parameters might include different optical elements chosen for a given imaging channel. Particularly for fluorescence imaging, the image acquisition parameters become problematic due to variation in tissue type, sample preparation, disease state, and optical sensitivity of fluorescent probes. Some fluorescent labels are not as bright as other fluorescent labels, but longer excitation may actually only photobleach the probes.

The plurality C of imaging channels may have a number from about 2 to about 100, depending on the type of imaging. The imaging methods might include optical methods (e.g. bright field, scattering, fluorescence, phosphorescence, Raman, stimulated Raman, surface enhanced Raman, and others), mass spectrometric methods (e.g. mass cytometry, molecular ion beam imaging), or other methods for image generation, (including but not limited to electrical, mechanical, acoustic, and magnetic methods). For example, if mass spectrometry imaging is performed, the available molecular weight spectrum for detection of ionic labels can include a molecular weight up to about 2000 Da. It may then be possible to have up to 100 distinct labels, requiring 100 imaging channels to independently contrast each label. For fluorescent labelling, while there may be up to 20 separate imaging wavelength filters/ranges. More than one probe may be detected within a single wavelength range, by specifically capturing each wavelength and assigning false color. Alternatively, combinations of fluorescent labels can be used as one label and analysis to detect dual emitting pixels and computationally assigned to the appropriate probe. Accordingly, C may be a number from about 2 to about 30, about 2 to about 20, or about 2 to about 10 biomarkers being interrogated.

The method further includes selecting a plurality D of contrast thresholds, wherein the plurality D of contrast thresholds includes at least one ratio having a value differing by one or more order of magnitude from values of the ratios of a remainder of the plurality D; selecting a plurality E of thresholds of marker positivity, wherein the plurality E includes at least one threshold having a value differing by one or more magnitudes from values of a remainder of the plurality E; and generating a third plurality of slide images, by analyzing the second plurality of slide images at each of the plurality D of contrast thresholds and at each of the plurality E of thresholds of marker positivity, wherein the third plurality of slide images comprises an A×B×C×D×E number of slide images. The method further includes ranking each of the third plurality of slide images, thereby producing a ranked order plurality of Whole Slide Image data.

The plurality D of contrast thresholds may include one or more contrast thresholds which differ from each other by at least 1 order of magnitude, e.g. a factor of ×10, at least 3 contrast thresholds, differ from each other by at least two orders of magnitude, e.g., a factor of ×100; or may be about 4 to 5 ratios differing by at least 3 orders of magnitude, e.g. ×1000. In some examples, the plurality D of contrast thresholds may include 4 to 5 thresholds differing by at least 1 order of magnitude.

The plurality E of thresholds of marker positivity may include at least two levels of threshold differing from each other by at least one order of magnitude; at least three levels of marker positivity threshold, a set of three levels ranging over two orders of magnitude, or 4 to 5 levels where the set of 4 to 5 levels range over at least two orders of magnitude. In some examples, the plurality E of thresholds of marker positivity comprises at least one threshold having a value differing by one or more magnitudes from values of a remainder of the plurality E.

Generating the second plurality of slide images may include analyzing the first plurality of slide images at each of the plurality, D, of contrast thresholds and at each of the plurality, E, of thresholds of marker positivity.

Adaptive data compression may add an additional factor of optimization. In some examples, the method may further include selecting a plurality F of data compression values, wherein generating the third plurality of slide images includes analyzing the second plurality of slide images at each of the plurality F of data compression values, thereby generating the third plurality of slide images, wherein the third plurality comprises an A×B×C×D×E×F number of slide images. The plurality F of data compression values may include at least three data compression values differing from each other by at least a factor of two, at least a factor of four, or at least a factor of eight. For example, the data compression value may be selected to reduce the data by a factor of two, by combining the data of every second pixel, averaging the data of every second pixel, or dropping the data of every second pixel, or any other data compression process as is known in the art. Variations in compression level may allow the histologist or pathologist to judge if data quality is sufficient to utilize a maximal compression value without loss of critical data to permit cloud sharing of data.

In some examples, ranking may include reducing a number of the third plurality of slide images to be less than the A×B×C×C×D×E number of slide images, thereby producing an optimized plurality of slide images. In other variations, ranking may include reducing the number of the third plurality of slide images to be less than the Ac B×C×D×E×F number of slides images to produce an optimized plurality of slide images. In some examples, ranking may be performed automatically. The reduced set of images may be the set of images presented to the user, where the user may choose which images/parameters he/she finds optimal. The user may also decide whether optimized parameters may be used for image collection for a specific sample or set of samples or image collection for the specific sample or set of samples should be made with the universal standard set of parameters. In some examples, images representing each of the two slide image sets may be presented side-by-side for ease of review.

As mentioned above, when optimized parameters may be advantageous, the method further includes selecting a subset of imaging and analysis parameters selected from one or more of the plurality B of image acquisition parameters; the plurality C of imaging channels; the plurality D of contrast thresholds; the plurality E of thresholds of marker positivity; and any combination thereof. In some examples, a sub-set of the plurality F of data compression values may be selected to obtain an optimized plurality of data compression values. The sub-sets selected may be based upon the viewed ranked images and correlating the parameters provided optimal (parameters to be kept within the sub-set) or non-optimal (parameters to be discarded or sought to be modified). Selecting the sub-set of the imaging parameters may thereby provide an optimized plurality of imaging and analysis parameters for the one or more samples.

In some examples, image collection as described above may be repeated using the optimized plurality of data compression values F; the optimized plurality of imaging parameters B, and/or the different selected size for each of the plurality A of imaged regions. The optimized plurality of data compression values F; the optimized plurality of imaging parameters B, and/or the different selected size for each of the plurality A of imaged regions selected for repeating the image collection may be centered around the best of the plurality of ranked-ordered images to produce a plurality of improved WSI data. This process may be performed iteratively to obtain successive sets of improved WSI data. In some examples, only one improved value of A, B, C, D, E, F, or G is used when obtaining the improved WSI data. In other variations, more than one improved values of the values of A, B, C, D, E, F, or G are used, In some examples, 2 or more sets of images may be collected for each sample of the one or more samples, where a first set of images is collected using a standardized set of imaging and analysis parameters and a second set of images is collected using the optimized set of imaging and analysis parameters for the one or more samples. In some examples, the first set of images may be compared to the second set of images, thereby determining a degree of sameness. The degree of sameness may be employed to revise the optimized set of imaging and analysis parameters to provide a further optimized set of imaging and analysis parameters for another further refined set of image collection for the one or more samples. Optimized parameters may be iteratively improved in successive cycles of ranking and image generation and analysis.

In some examples, metadata of each of the one or more samples may be associated with the third plurality of slide images produced by the image collecting. In some examples, staining parameters used for each of the one or more samples may be associated with the third plurality of slide images produced by the image collecting. In some examples, the tissue type of each of the one or more samples may be associated with the third plurality of slide images.

Another element that is typically not optimized in the context of the entire workflow is the staining itself. Typically, during assay development staining is optimized by sequential exploration of conditions that lead to images that are viewed as "good" by the end user; typically this requires multiple iterations of staining, all under identical acquisition and analysis conditions. In some examples, one would explore the impact of staining at the same time as parameters A, B, C, D, E and F.

Depending on the system used, the concentration of signal-generating entity (e.g. fluorophore, mass tag, etc.) associated with a particular marker depends on 2-5 different staining parameters. For example, in systems where detection is based on fluorophores associated with secondary antibodies, the amount of signal (for a given amount of biomarker or target expressed) depends on the amount of primary Ab bound to target, the amount of secondary antibody bound to primary antibody, and the number of fluorescent labels (on average) per secondary antibody. Typically, in the later stages of assay development, the number of fluorophores per secondary Ab is fixed, as is the choice of primary Ab (and therefore its affinity to the target). Thus the parameters that can be varied are the staining concentration of the primary antibody, and the staining concentration of the secondary antibody. Thus, there is a set of conditions G associated with the various concentrations.

For fluorescent systems where there is enzymatic amplification of one or more components amongst the detection reagents, and also in systems where the fluorophore is not built into a secondary antibody, there are additional parameters to vary (e.g. enzyme concentration, enzymatic amplification time, fluorophore concentration, etc. In short, there may be a plurality of staining conditions G that define staining "quality" where G may be from about 2 to about 20, about 3 to about 40, about 4 to about 60 staining parameters or more. In fluorescent systems having multiplex fluorophores, where some or all of the fluorophores are not built into a secondary antibody, there may be more than 60, more than 80 or more than 100 staining quality parameters G. Therefore there may be a plurality of WSI data having A×B×C×D×E×F×G different images from which optimal conditions are elucidated. In some examples, the process of staining the slides employing the "G" staining quality parameters may be automated.

In some examples, the method may be performed automatically by computer-executable instructions.

Non-Transitory Computer-Readable Medium.

In another aspect of the invention, a non-transitory computer-readable medium is provided in which a program is stored for causing a processor to perform a method for generating Whole Slide Image (WSI) data for one or more samples, including: selecting a plurality of A of imaged regions from one or more samples; selecting a plurality B of image acquisition parameters for each of a plurality C of imaging channels; acquiring a plurality of first slide images for each of the one or more samples at each of the plurality B of image acquisition parameters and at each of the plurality C of imaging channels, wherein the first plurality of slide images includes an A×B×C number of images; selecting a plurality D of contrast thresholds; selecting a plurality E of thresholds of marker positivity, generating a second plurality of slide images, by analyzing the first plurality of slide images at each of the plurality D of contrast thresholds and at each of the plurality E of thresholds of marker positivity, where the second plurality of slide images includes an A×B×C×D×E number of slide images; and ranking each of the third plurality of slide images, thereby producing a ranked order plurality of Whole Slide Image data. The non-transitory computer-readable medium may further execute the method which includes selecting a plurality F of data compression values, wherein generating the third plurality of slide images further comprises analyzing the first plurality of slide images at each of the plurality F of data compression values, thereby generating the second plurality of slide images, wherein the third plurality comprises an A×B×C×D×E×F number of slide images. The method executed by the on-transitory computer-readable medium may have any of the steps of the methods described herein and incorporate any of the features thereof.

EXAMPLES

Figure 6:
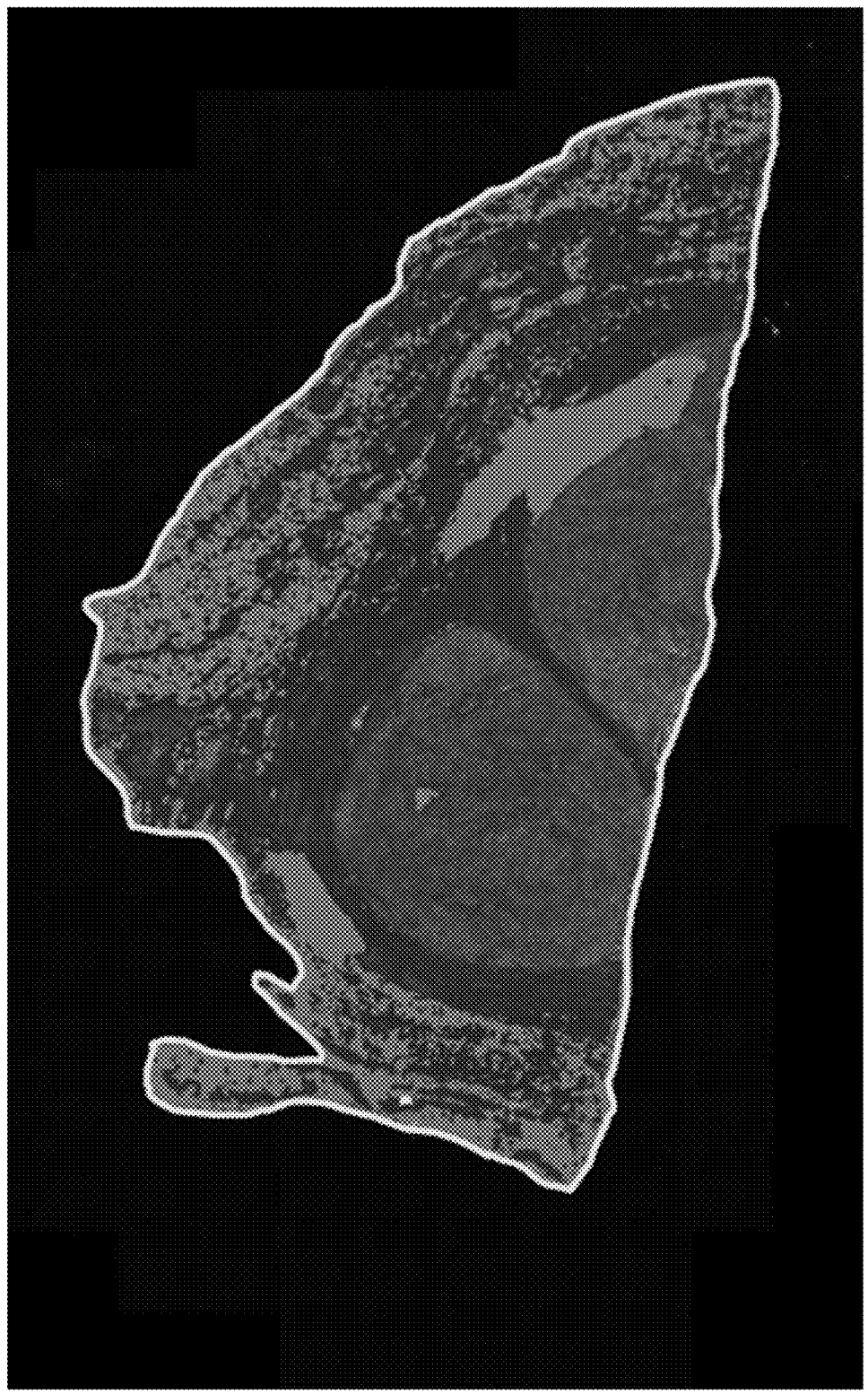
FIG. 6 shows one example of a stained slide that may be part of set of stained slides (e.g., sections) of a tissue sample that may be examined as described herein.

A series of 10 formalin-fixed, paraffin embedded (FFPE) tissue sections (approximately 4-5 μm thick) and two control slides were processed as described herein and compared with traditionally processing methods. The results show an improvement in the processing time as well as quality of the final data. The sections were obtained from 5 melanoma tumor blocks, with 2 serial sections per tumor. The control slides comprised tonsil and melanoma. Typical average sizes for the sections were 2.25 cm²±0.75 cm². Each section had a complex shape (i.e. non-rectangular). An example is shown in FIG. 6. In FIG. 6 just one stained slide of a set of stained slides of the tissue sample is shown. In practice the set may include a plurality of (e.g., 5 or more, 10 or more, 15 or more, 20 or more 30 or more, 50 or more, etc.) stained slides.

The samples were stained using a commercially available Ultivue Ultimapper PD-L1 kit, using established protocols on a Leica Bond RX auto-stainer instrument. The Ultivue PD-L1 kit comprises the following labelled antibody reagents/fluorescence detection channels. Stains were used (thus five channels): DAPI (staining for nuclei)/DAPI channel (purple-blue in images); anti-CD8 (staining for CD8)/FITC channel (green in the images); anti-CD68 (staining for CD68)/TRITC channel (yellow in the images); and anti-PDL1 (staining for PD-L1)/Cy5 channel (red in the images); and a mixture of anti-cytokeratin & anti-Sox10 (staining for pancytokeratin and Sox 10)/Cy7 (cyan in the images). Note that SOX10 is a nuclear transcription factor shown to be a sensitive and specific marker of melanoma, while panCK is associated specifically with carcinoma. Thus, given that the samples are all melanoma, only SOX10 is present. In this example, imaging was carried out on a Zeiss Axioscan Z1 instrument using a Colibri light source. Indica Labs Halo 3.0 software was adapted for use with the methods described herein.

Once the samples had been stained and images acquired, the samples were processed using the method described herein (and discussed in greater detail below). In addition, the samples were also processed using traditional processing methods, for comparison. Traditional ("standard") analysis protocols used on melanoma tissue samples that have been stained with the Ultivue PD-L1 kit using the Leica Bond Rx included cell segmentation, marker thresholding, software-based analysis batch processing (i.e. no operator time), and analysis quality control (QC). Starting values for the various parameters were input from previous analyses.

For the 10 (ten) melanoma whole-slide images acquired on the Zeiss and exported into Halo, the standard analysis method took a total of 45 minutes on further adjusting parameters associated with segmenting cells, 120 minutes on further adjusting parameters associated with thresholding the four protein-based markers, and 60 minutes on analysis QC of the resulting images. Part of this effort involved setting high and low thresholds for one particular marker (CD68) and reviewing the resulting masks over multiple slides. Image masks were generating in Halo using the final parameters, and cell counts were determined for the 10 samples. Values for the various finalized analysis parameters were given to the data set resulting from this standard analysis.

The methods described herein for generating image data (e.g., methods for defining global mask parameters from an extracted subset) were performed on the same data set for comparison. The analysis using the method described herein was carried out as follows. Two small regions of analysis (ROA), each 425 μm×425 μm, were chosen from just one of the unprocessed whole-slide fluorescence images from the microscope data set. The image (corresponding to a single slide) selected from the microscope data set may be selected at random, or it may be selected because it shows a minimum amount of staining in one or more (e.g., all or a subset of) channels. As described above, the plurality (in this example, 2) of image regions within the selected image (slide) may be chosen because they include one or more regions without significant cell staining (e.g., sparse regions) as well as one or more regions with substantial staining (e.g., densely stained). Thus, both sparse (or empty) regions as well as densely stained regions may be represented. A sparse and a densely stained region may be identified by the method or system described herein by generating a distribution of the staining (for one or more of the channels) over the selected image. For example, the image may be divided into smaller regions (e.g., 100×100 pixels, etc.), and identifying regions that are within the sparse end of the distribution (within about 5-10% of the low end of the spread of the distribution) to identify candidate sparse regions, and identify regions that are within about 80-95% of the 'dense' end of the distribution. The first of the plurality of imaged regions may be sparsely stained and a second of the plurality of imaged regions may be densely stained. Additional, intermediately stained regions may be selected as well, forming a total of "A" regions, as described above. In this example, a nuclear stain, such as DAPI, was used to select sparsely stained and densely stained regions. Selecting a variety of sparse and densely stained regions may assist in the choice of global segmentation and threshold analysis parameters to be used as described herein.

In this example, regions were chosen to be not proximate to one another within the selected slide, but to contain features exhibiting a higher density and a lower density of cells as just mentioned.

The ("A") of regions selected may be selected using a user interface allowing manual or semi-automatic selection, or they may be selected automatically. The shape and/or size of the regions selected may be arbitrary. In some examples the regions (which may also be referred to as subregions of the selected slide from the stained volume are 20% or less than the area/size of the area of the identified side. For example, the size of the identified area/size may be 18% or less, 15% or less, 12% or less, 10% or less, 8% or less, 5% or less, etc. of the size of the identified stained slide from the set of stained slides.

As mentioned above, five channels were used in the tissue sample forming the set of stained slides in this example. All five channels may be used for this analysis, or a subset of these stained channels may be used. For example, two of the channels may be used, so that the number of imaging channels used to generate the masks ("C") is 2; the blue/DAPI (nuclear stain) and green/anti-CD8 (FITC) channels may be used.

In addition, for each of these channels, thresholds may be determined. Specifically, for each channel, a number ("D") of variations of contrast thresholds may be identified. If only one variation is used, then D is 1; typically D may be greater than 2. In this example, for the blue (DAPI) channel, three variations of nuclear contrast threshold (NCT) may be identified. In practice, these thresholds may be manually, automatically or semi-manually determined. In the case of NCT, a low value (e.g., corresponding to greater number of pixels indicating nuclear staining), a high value (e.g., corresponding to a lower number of pixels indicating nuclear staining) and an intermediate value may be selected. Thus, for the first channel (of the two channels, C) there are three variations of contrast thresholds (D=3 for the first of two channels). For the second channel (e.g., FITC), only a single variation, e.g., a default value may be used (e.g., D=1 for the second of the two channels). Thus, the total array of variations of contrast thresholds in this example is 3*1 or 3.

One or more variations of a thresholds for marker positivity may also be chosen for each channel. For example, three variations of the minimum nuclear intensity (MNI) for the DAPI stained channel may be identified (e.g., E=3 for the first of 2 channels). For the second channel, e.g., the FITC channel, three variations of the FITC cytoplasm positive threshold (T) may be used (e.g., E=3 for the second of the two channels). Thus, the total array of variations of the thresholds for marker positivity may be calculated as 3*3 or 9. Although three variations are described, and may be automatically, manually or semi-automatically determined, multiple values for both the contrast thresholds and the positivity thresholds may be used, such as, e.g., 2, 3, 4, 5, 6, etc.

Thus, the total number of threshold variations identified is the product of the total array of variations of contrast thresholds (e.g., 3) and the total array of variations of the thresholds for marker positivity (e.g. 9), so a total of 27 variations are possible.

Optionally, each channel may also include additional variations of parameters such as variations of image acquisition parameters, B, which may further expand (by multiplying) the number of variations. Finally, other threshold variations may also be identified.

Returning to our example, three variation of the nuclear contrast threshold may be identified as, e.g., 0.504, 0.507 and 0.51. Generally, increasing the NCT setting will lead to a decrease in detection of the number of nuclear pixels. In our example, the three variations of minimum nuclear intensity (MNI) may be set, e.g., a0.052, 0.057 and 0.062. Generally, increasing the MNI will lead to detection of more weakly stained nuclei, while decreasing the setting will lead to fewer false positive identifications. T is used to set the minimum intensity for cytoplasm to be considered positive for the marker associated with FITC, in this case CD8. NCT and MNI will have a significant impact on the DAPI channel, both in the number of nuclei observed (and therefore also total number of cells) and also in segmentation among closely spaced cells. These parameters, in turn, will have an impact on all the other channels, since delineation of individual cells is necessary for counting the number of positive cells after thresholds are set in each channel.

Note that while only these three threshold parameters (a total of 27 variations) were chosen for this example, many other parameters could be varied, and/or additional variations for each parameter may be included, each of which may impact the resulting image quality. Surprisingly, these parameters have been found by this analysis to be not orthogonal (i.e., has interaction with other variables, including across different channels). These include but are not limited to thresholds for additional channels of fluorescence, nuclear segmentation aggressiveness, nuclear size, cell size, the maximum cytoplasm radius, and so on.

The values of the variations examined as part of this example may be based on historical values or other best-guess values. Alternatively an approximate estimate may be determined by analyzing the chosen slide image. As mentioned above, values may be approximated by a machine learning agent trained on a database that is built using the traditional technique. From these starting values, an increased and decreased value may be chosen for each parameter (the alternative variations).

A set of masks may then be generated for each of these different variations, and for each sub-region from the selected stained slide (e.g., 2 subregions). As mentioned above, the combination of 3 settings for each parameter having three variations of different parameters led to generation of 27 different candidate masks for each ROA, for a total of 54 candidate masks (27×2). Each mask may include two layers (e.g., the selected channels from the five different optical channels).

Masks may be formed by applying the parameter variations (thresholds) for each of the selected channels of each of the subregions towards segmentation of the cells within the subregions. Segmentation using these parameters may be performed in any appropriate manner, such as, for example, region-based segmentation, edge-detection segmentation, segmentation based on clustering (e.g., K-means segmentation), dual clustering, mask R-CNN segmentation, etc. In some examples segmentation may be done using a machine learning agent. For example, a database of curated images, and in particular florescent images of cells, may be used to train a machine learning agent to identify cells. In one example, HALO segmentation (e.g., a trained network) was used. The parameter variations modify the segmentation technique used. Thus, for each combination of variations and each sub-region, a different "mask" showing cell outlines formed by segmentation of the sub-region applying the parameter variations may be generated.

This will result in a set of masks, numbering the product of the number of sub-regions (e.g., 2) times the number of parameter combinations for each selected channel (e.g., 27). Thus, in this example, 54 different masks may then be generated and reviewed, so that they may then be manually, automatically or semi-automatically rank ordered based on a comparison with the original image. For example in some examples a ranking machine-learning agent may be used, following training on a curated dataset. In manual or semi-automatic systems, the system may provide a side-by-side comparison of the original image sub-region to each of the masks generated, asking a reviewer to confirm (or enter) a ranking score.

Figure 7B:
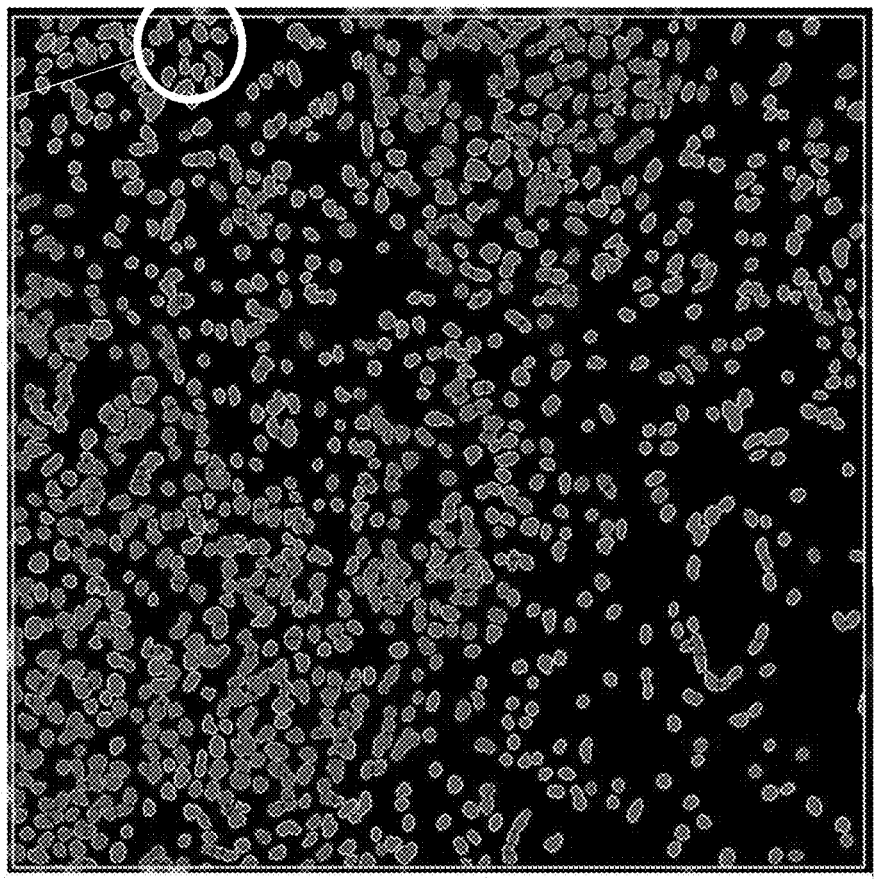
FIG. 7B is an example of a mask identifying cells (circled) using a particular set of parameters as described herein.
Figure 7A:
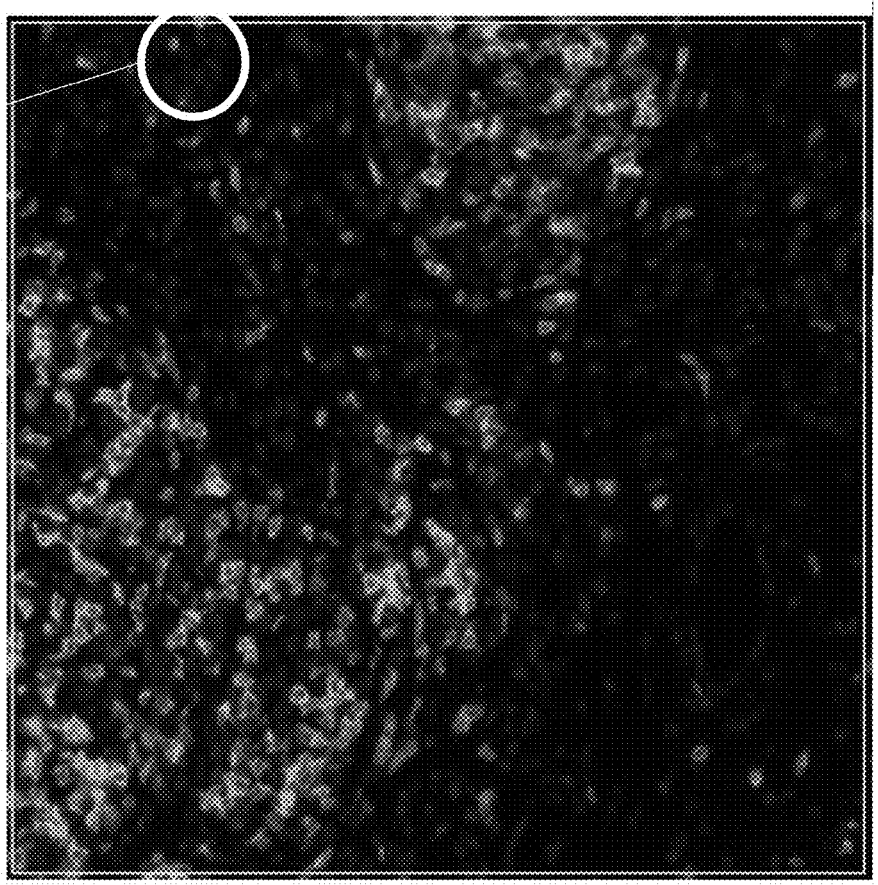
FIG. 7A shows a first sub-region of a slide (e.g., the slide of FIG. 6) in two channels (blue and green).
Figure 8B:
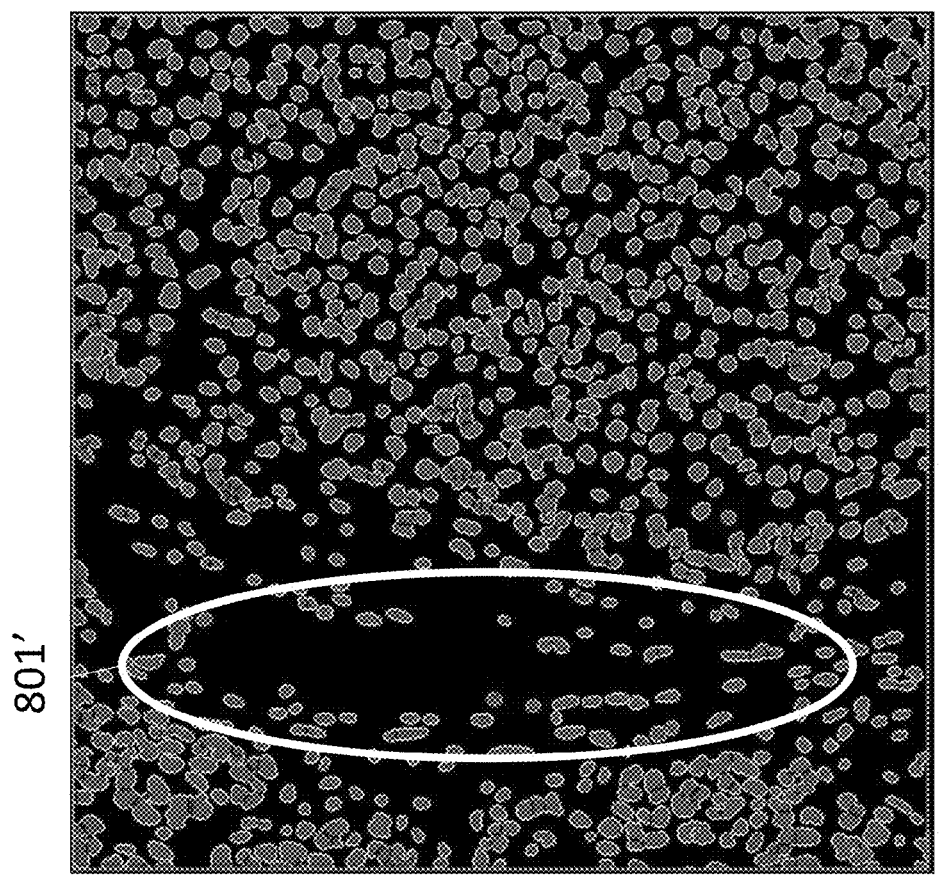
FIG. 8B is an example of a mask identifying cells (circled) using a particular set of parameters as described herein.
Figure 8A:
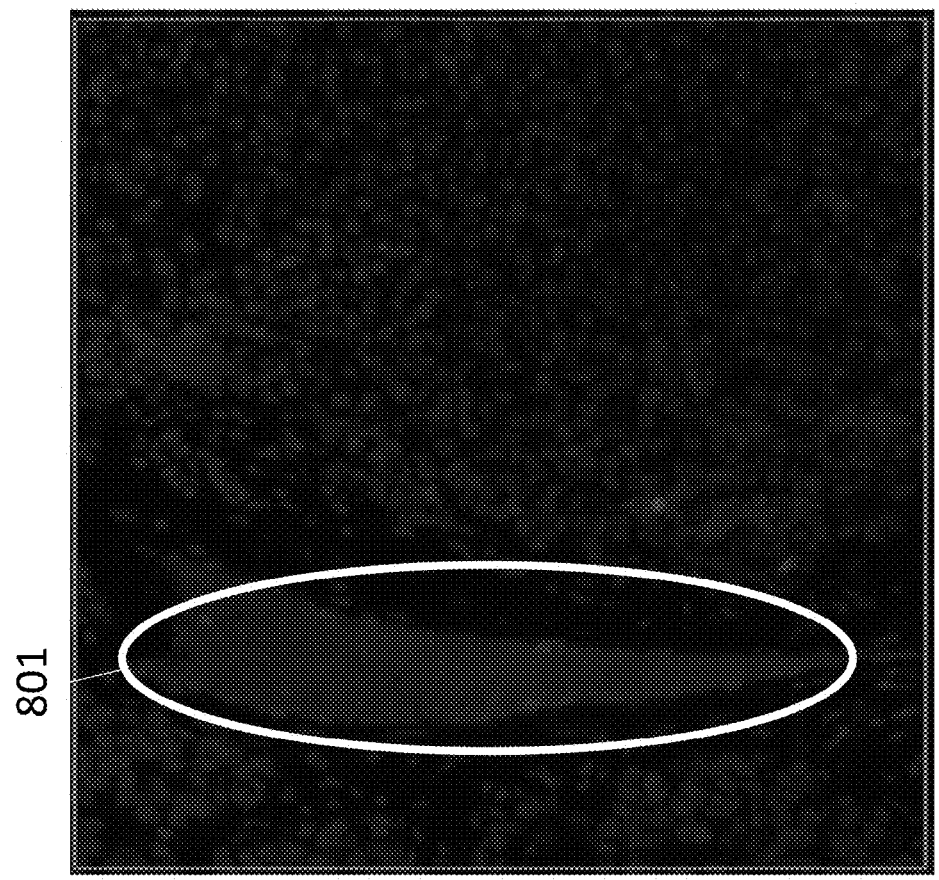
FIG. 8A shows a second sub-region of a slide (e.g., the slide of FIG. 6) in two channels (blue and green).

In the example above, two different reviewers independently ranked the quality of resulting 54 masks, based on positive and negative correlation to the original images. More specifically, the original ROA image (in two colors, DAPI and FITC) was compared alongside each 2-color mask. FIGS. 7A and 7B shows a representative example of a comparison between the original slide region (FIG. 7A, showing the two channels selected) and a mask (FIG. 7B, showing the two channels selected) from ROA #1, with highlighted regions 701, 701' illustrating features that are poorly correlated to the original with the mask. Poor correlation can result from either missing cells completely, or not registering fluorescence from a mask. FIGS. 8A-8B shows representative comparison between the original slide region (FIG. 8A, showing the two channels selected) and a mask (FIG. 8B, showing the two channels selected) from ROA #2, with highlighted regions illustrating features that are correctly identified as having no FITC-positive cells, or mis-identified as having FITC-positive cells. The masks shown in FIGS. 7B and 8B are examples using different variations of the parameters.

Figure 9B:
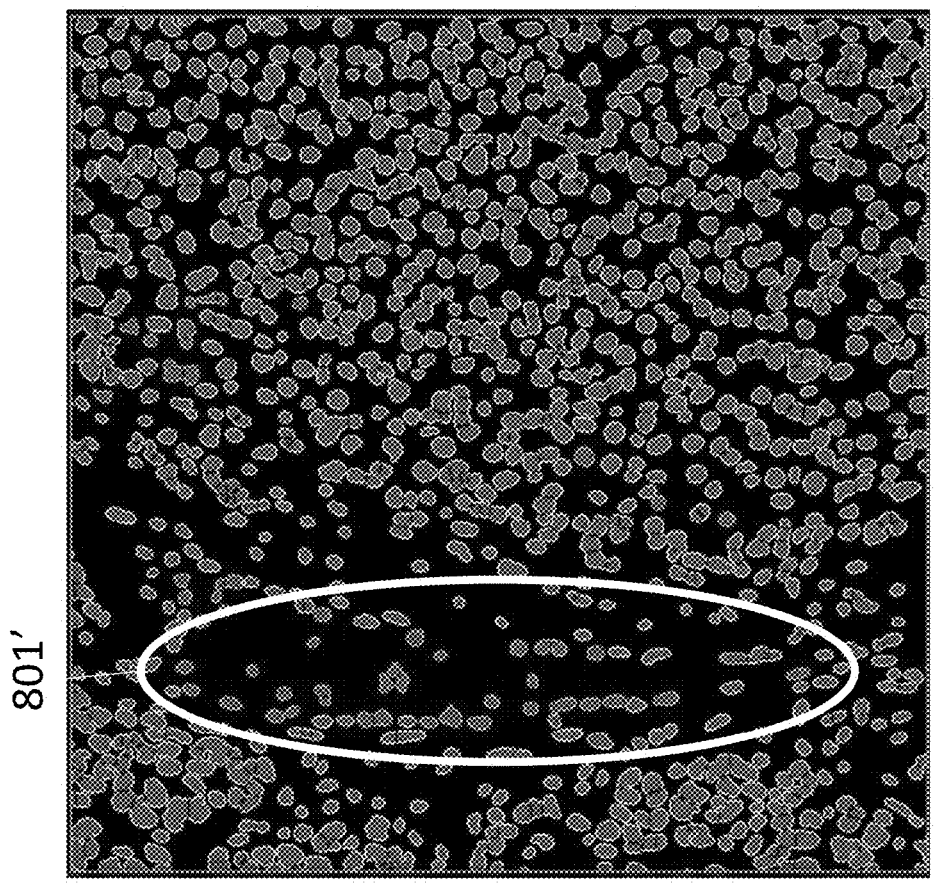
FIGS. 9A-9B show another example of the second sub-region of the slide (FIG. 9A), with a side-by-side comparison to another example of a mask (FIG. 9B) generated as described herein.
Figure 9A:
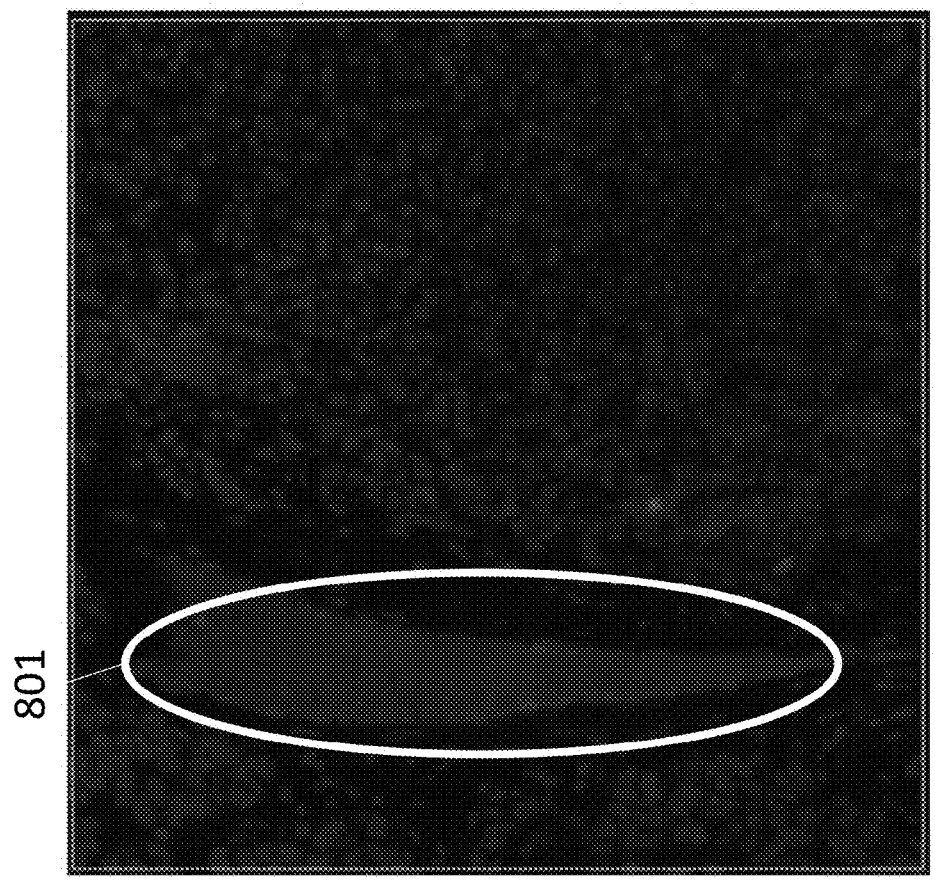

FIG. 8B shows an example of a relatively "good" mask that may be ranked relatively high. FIG. 9B shows an example of a relatively "bad" mask, that may be ranked lower. The ranks of all of the masks (including reference to the combination of parameters generating each mask) may then be rank ordered. FIGS. 10A-10C illustrates an example showing side-by-side comparison of different masks for the first sub-region (ROA #1). FIG. 10A shows the original sub-region (ROA #1) of the slide, while FIGS. 10B and 10C show relatively better and worse masks, respectively. FIGS. 11A-11C illustrates an example showing side-by-side comparison of different masks for the second sub-region (ROA #2).

Table 1 in FIG. 12 shows the analysis of some of the 54 masks by Reviewer #1. Based on the criteria descried above, Reviewer #1 ranked the top 5 best (light highlight) and bottom 5 worst (darker highlight) for each ROA. Reviewer #2 independently carried out the same task, and based on the combined analysis, mask #18 was chosen as the best set of parameters.

These values may then be applied to the entire set of slides. If other channels are to be reviewed, values for parameter thresholds may be either derived from the resulting parameters (and therefore cell detection) or may be set independently, e.g., using the values provided by the supplier (e.g., staining supplier), staining machinery and/or literature, without the need for any further adjustment or optimization. Thus, in this example, whole-slide masks were generated for the slide containing the 2 ROA's and also for the remaining 9 slides in the set of stained slides. In this example, each slide has approximately 1000 fields of view (FOV), thus there are a total of 10,000 FOV (10 slides×1000 FOV/slide), and five layers for each FOV, for a total of 50,000 images. The method described herein therefore allowed a huge time and processing (and therefore cost) savings compared to other known methods. In this example, the final masks for were generated from final mask parameters by close inspection and optimization of only two (2) of the 10,000 FOV, and only two of the layers, based on a total of 4 images (and 54 reviewed masks/images). This process led to a significant savings in time. Further, this technique did not require any dedicated quality control (QC), providing an additional time savings.

The results of the technique described above were as good or better when compared to existing analysis methods and systems in the final statics taken from the image data for the tissue sample and were performed at a significant time and processing savings. In total, the example described above, based on a semi-manual implementation of this method, required only an hour for each reviewer, e.g., a total of 30 minutes on segmentation and 30 min on thresholding of the FITC channel. In comparison, the traditional method that was also performed on the same dataset required almost four hours (per reviewer, when performed in duplicate).

The masks resulting from the example method described above were extremely similar, to the untrained eye, statistically, and to the trained eye. The images look similar in terms of the number of cells, and the phenotype of each cell (which color or colors). This was borne out statistically as well in analyses of whole slides. Table 2 in FIG. 13 shows a series of outputs after mask generation. The parameters shown in the table are a subset of the entire output but represent important parameters. As shown in FIG. 13, the percentage of positive cells (above threshold) for each of the four protein markers, in tumor and non-tumor cells, for two different whole slide samples, comparing the traditional method (Group A) and the improved method described herein (Group B).

As shown, the markers fall into two categories: adjusted parameters and blind fit. The adjusted parameters related to CD8 (FITC channel), since FITC cytoplasm positive threshold (T) was one of the parameters varied. The remaining six parameters were set by Group A and incorporated as-is by Group B without any optimization or quality control of ensuing images. The data indicate that the quantitation of positive cells for the protein markers on a percentage basis vary little between Group A and Group B. The two samples represent very different types of tumor tissue: in Sample 188-1, a high percentage of the cells are "hot" (a high amount of CD68 and PD-L1), while sample 460-24 are considered "cold" (small amounts of CD68/PD-L1). Nevertheless, the percentages of each phenotype do not vary significantly between Group A and Group B, including for the 6 phenotypes corresponding to the 3 markers for which neither thresholding nor reviewing was carried out by Group B.

These results were verified independently by a pathologist. An expert in multiplexed immunofluorescence in tissue samples reviewed and compared the 20 masks generated (10 pairs, each pair with the Group A and Group B mask). The expert was not informed in advance which masks corresponded to Group A and which to Group B. The expert found additional cells in certain fields of view within the tumor area on the masks generated by Group A. However, as shown above, such differences are statistically meaningless when multiple fields of view are considered, since overall, the number of positive cells found by each group were very similar, and in some cases the Group B masks identified more positive cells. More importantly, in multiple cases the expert found that the Group A masks had problematic segmentation in that groups of cells were not successfully distinguished, but considered by the mask to be "giant single cells" and likewise that Group A masks consistently generated "ghost cells". Surprisingly, the review provided additional validation that the improved approach described herein (Group B) for parameter optimization was superior. This was particularly surprising, given that only a small number of sub-regions and channels (e.g., two colors) were used, representing an infinitesimal percentage of the overall data package (4 out of 50,000). Further, only three parameters were chosen (out of a dozen available), and only three variations were picked for each. Since the settings are continuous (e.g. 0 to 100%), a much larger number could have been chosen, e.g. 5 or 10 values for each parameter. Finally, the sub-regions chosen were not regions that would normally be considered interesting for determining the pathology of the tissue; instead these two regions were chosen because they had a high degree of difference (e.g. a region with low information content and a high degree of information content were chosen). At least one region was chosen as including areas where there should be no cells (e.g. lumens, blood vessels, epidermis surface, intracellular matrix, which might be considered a control).

Figure 14:
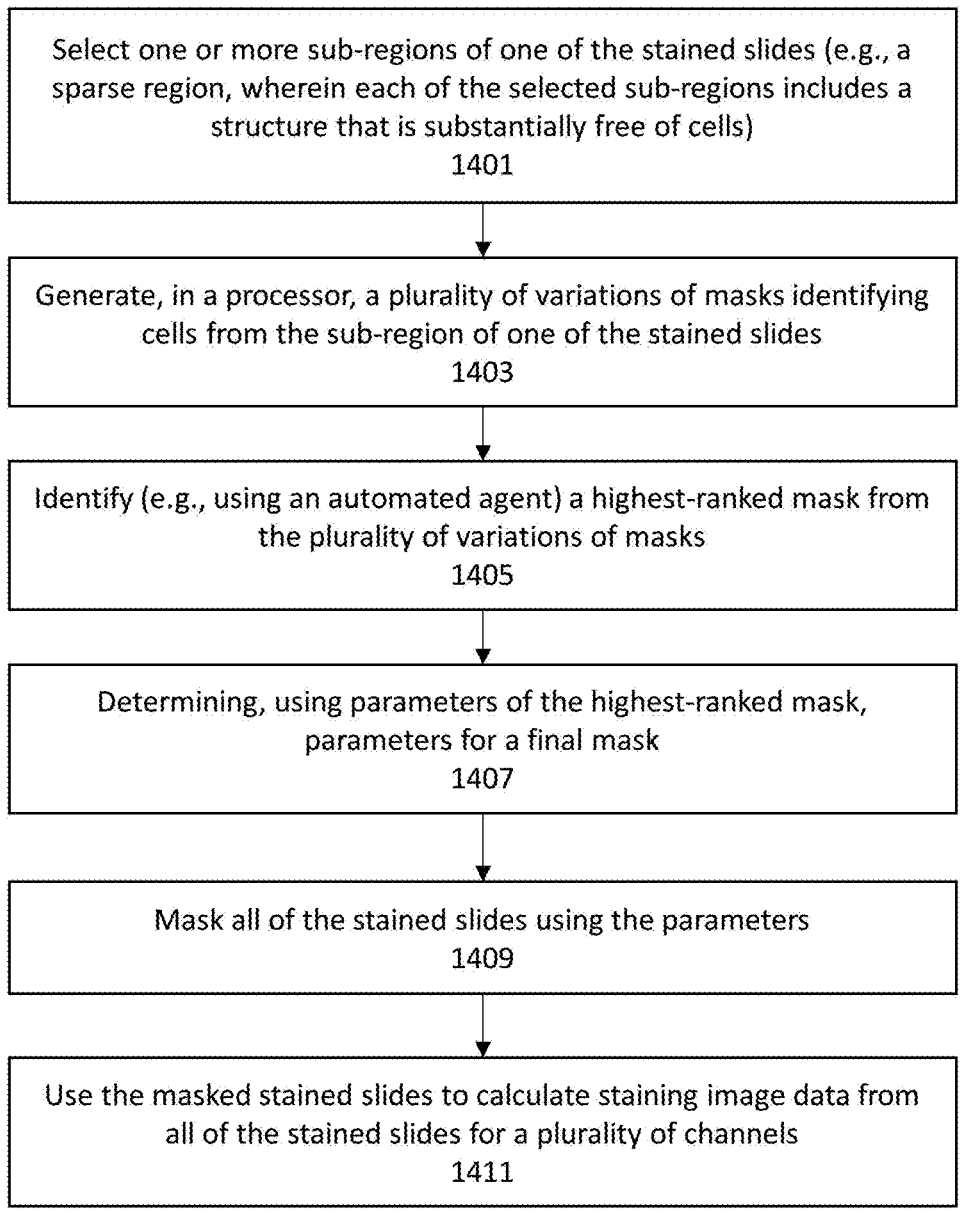
FIG. 14 illustrates one example of a method for analyzing a stained set of slides as described herein.

FIG. 14 illustrates another example of a method for generating image data for a set of stained slides that comprises a tissue sample. This may be an automated method, e.g., using a machine learning agent, as described above. For example, the method (or a system for performing the method) may include selecting one or more sub-regions of one of the stained slides, wherein each sub-region includes a structure that is substantially free of cells 1401. The method or system may then generate, in a processor, a plurality of variations of masks identifying cells from the sub-region of one of the stained slides 1403. The system or method may then identify, using an automated agent, a highest-ranked mask from the plurality of variations of masks 1405. The system or method may determine, using parameters of the highest-ranked mask, parameters for a final mask 1407 and mask all of the stained slides using the parameters 1409. Finally the system or method may use the masked stained slides to calculate staining image data from all of the stained slides for a plurality of channels 1411. A system for performing this method may include: one or more processors; a memory coupled to the one or more processors, the memory configured to store computer-program instructions, that, when executed by the one or more processors, perform a computer-implemented method comprising: generating, in a processor, a plurality of variations of masks identifying cells or regions of cells from a sub-region of one of the stained slides; identifying, using an automated agent, a highest-ranked mask from the plurality of variations of masks; and determining, using parameters of the highest-ranked mask, parameters for a final mask; masking all of the stained slides using the parameters; and using the masked stained slides to calculate staining image data.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

What is claimed is:

1. A method for generating image data for a set of stained slides that comprises a tissue sample, the method comprising:
    selecting a plurality of sub-regions from one of the set of stained slides;
    identifying, for each imaging channel of a first plurality of imaging channels, either a first number of variations of contrast thresholds, a first number of variations of thresholds of marker positivity, or a first number of variations of contrast thresholds and a first number of variations of thresholds of marker positivity, wherein each imaging channel is associated with a corresponding biomarker or plurality of biomarkers;
    generating a plurality of masks for each of the plurality of sub-regions corresponding to each combination of the variations of contrast thresholds and variations of thresholds of marker positivity for each imaging channel of the first plurality of imaging channels, wherein each mask is segmented to identify cells;
    ranking the plurality of masks based on an ability of each of the plurality of masks to accurately identify cells that are positive for the corresponding biomarker or plurality of biomarkers of each imaging channel of the first plurality of imaging channels;
    selecting a set of final mask parameters from the plurality of masks based on the rankings; and
    generating a set of slide images for all slides of the set of stained slides using the set of final mask parameters.

2. The method of claim 1, wherein selecting the plurality of sub-regions from one of the set of stained slides comprises selecting the sub-regions so that at least one of the sub-regions includes a structure that is substantially free of cells.

3. The method of claim 1, wherein identifying further comprises identifying a number of variations of image acquisition parameters for each imaging channel of the first plurality of imaging channels.

4. The method of claim 1, further comprising selecting a plurality of data compression values.

5. The method of claim 1, wherein the ranking is performed by a trained network.

6. The method of claim 1, further comprising iterating the steps of identifying and generating for different imaging channels.

7. The method of claim 1, further comprising determining, from the set of stained slides, statistics on labeled cells for a second plurality of imaging channels that is larger than the first plurality of imaging channels.

8. The method of claim 1, wherein selecting the plurality of sub-regions from one of the set of stained slides comprises selecting a different size for each of the sub-regions.

9. The method of claim 1, wherein each mask is segmented to identify cells using the variations of contrast thresholds and the variations of thresholds of marker positivity.

10. A method for generating image data for a set of stained slides that comprises a tissue sample, the method comprising:
    selecting a plurality of sub-regions from one of the set of stained slides, wherein at least one of the sub-regions includes a structure that is substantially free of cells;
    identifying, for each imaging channel of a first plurality of imaging channels: a first number of variations of contrast thresholds, a first number of variations of thresholds of marker positivity, or a first number of variations of contrast thresholds and a first number of variations of thresholds of marker positivity, wherein each imaging channel is associated with a corresponding biomarker or plurality of biomarkers;
    generating a plurality of masks comprising a mask for each of the plurality of sub-regions corresponding to each combination of the variations of contrast thresholds and the variations of thresholds of marker positivity for each imaging channel of the first plurality of imaging channels, wherein each mask is segmented to identify cells using the variations of contrast thresholds and the variations of thresholds of marker positivity;
    ranking the plurality of masks based on an ability of each of the plurality of masks to accurately identify cells that are positive for the corresponding biomarker or plurality of biomarkers of each imaging channel of the first plurality of imaging channels;
    selecting a set of final mask parameters from the plurality of masks based on the rankings; and
    generating a set of slide images for all slides of the set of stained slides using the set of final mask parameters.

11. A system for generating image data for a set of stained slides that comprises a tissue sample, the system comprising:
    one or more processors;
    memory coupled to the one or more processors, the memory configured to store computer-program instructions, that, when executed by the one or more processors, perform a computer-implemented method comprising:
selecting a plurality of sub-regions from one of the set of stained slides;
identifying, for each imaging channel of a first plurality of imaging channels, either a first number of variations of contrast thresholds, a first number of variations of thresholds of marker positivity, or a first number of variations of contrast thresholds and a first number of variations of thresholds of marker positivity, wherein each imaging channel is associated with a corresponding biomarker or plurality of biomarkers;
generating a plurality of masks for each of the plurality of sub-regions corresponding to each combination of the variations of contrast thresholds and variations of thresholds of marker positivity for each imaging channel of the first plurality of imaging channels, wherein each mask is segmented to identify cells;
ranking the plurality of masks based on an ability of each of the plurality of masks to accurately identify cells that are positive for the corresponding biomarker or plurality of biomarkers of each imaging channel of the first plurality of imaging channels;
selecting a set of final mask parameters from the plurality of masks based on the rankings; and
generating a set of slide images for all slides of the set of stained slides using the set of final mask parameters.

12. The system of claim 11, wherein selecting the plurality of sub-regions from one of the set of stained slides comprises selecting each of the sub-regions so that each sub-region includes a structure that is substantially free of cells.

13. The system of claim 11, wherein identifying further comprises identifying a number of variations of image acquisition parameters for each imaging channel of the first plurality of imaging channels.

14. The system of claim 11, further comprising selecting a plurality of data compression values.

15. The system of claim 11, wherein the ranking is performed by a trained network.

16. The system of claim 11, further comprising iterating the steps of identifying and generating for different imaging channels.

17. The system of claim 11, further comprising determining, from the set of stained slides, statistics on labeled cells for a second plurality of imaging channels that is larger than the first plurality of imaging channels.

18. The system of claim 11, wherein selecting the plurality of sub-regions from one of the set of stained slides comprises selecting a different size for each of the sub-regions.

19. The system of claim 11, wherein each mask is segmented to identify cells using the variations of contrast thresholds and the variations of thresholds of marker positivity.

* * * * *